US009073963B2

(12) United States Patent
Peri et al.

(10) Patent No.: US 9,073,963 B2
(45) Date of Patent: Jul. 7, 2015

(54) PEPTIDES AND PEPTIDOMIMETICS USEFUL FOR INHIBITING THE ACTIVITY OF PROSTAGLANDIN $F_{2\alpha}$ RECEPTOR

(75) Inventors: Krishna Peri, Saint-Laurent (CA); Felix Polyak, Montréal (CA); William Lubell, Montreal (CA); Eryk Thouin, Montréal (CA); Sylvain Chemtob, Montreal (CA)

(73) Assignees: Universite De Montreal, Montreal (CA); Theratechnologies, Inc., Saint Laurent (CA)

( * ) Notice: Subject to any disclaimer, the term of this patent is extended or adjusted under 35 U.S.C. 154(b) by 431 days.

(21) Appl. No.: 12/423,975

(22) Filed: Apr. 15, 2009

(65) Prior Publication Data
US 2012/0172318 A1 Jul. 5, 2012

Related U.S. Application Data

(63) Continuation of application No. 10/517,687, filed on Dec. 10, 2004, now Pat. No. 7,521,530.

(30) Foreign Application Priority Data

Jun. 11, 2003 (WO) .................. PCT/CA03/000903

(51) Int. Cl.
*C07K 7/06* (2006.01)
*A61K 38/00* (2006.01)

(52) U.S. Cl.
CPC .. *C07K 7/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,330,440 A | 5/1982 | Ayers et al. | |
| 4,522,752 A | 6/1985 | Sisto et al. | |
| 5,440,013 A * | 8/1995 | Kahn | 530/317 |
| 5,475,085 A * | 12/1995 | Kahn | 530/317 |
| 5,508,384 A | 4/1996 | Murphy et al. | |
| 5,618,914 A * | 4/1997 | Kahn | 530/317 |
| 5,670,155 A * | 9/1997 | Kahn | 424/208.1 |
| 5,672,681 A * | 9/1997 | Kahn | 530/317 |
| 5,674,976 A * | 10/1997 | Kahn | 530/317 |
| 5,955,575 A | 9/1999 | Peri et al. | |
| 6,300,312 B1 | 10/2001 | Chemtob et al. | |
| 7,521,530 B2 * | 4/2009 | Peri et al. | 530/329 |
| 2012/0172318 A1 * | 7/2012 | Peri et al. | 514/21.7 |

FOREIGN PATENT DOCUMENTS

| | | |
|---|---|---|
| EP | 0045665 | 9/1985 |
| WO | 9309104 | 5/1993 |
| WO | 9500551 | 1/1995 |
| WO | 9623225 | 8/1996 |
| WO | 9932640 | 7/1999 |
| WO | 0017348 A | 3/2000 |

OTHER PUBLICATIONS

Lombart and Lubell 1996 J. Org. Chem. 61: 9437-9446.*
Gosselin and Lubell 1998 J. Org. Chem. 63:7463-7471.*
Polyak and Lubell 1998 J. Org. Chem. 63: 5937-5949.*
Gosselin and Lubell 2000 J. Org. Chem. 2163-2171.*
Hannessian at al. 1997 Tetrahedron 53: 12789-12854; (specif. review of azabicyclo[X.Y.O]alkanone amino acids).*
Aube, J. In Advances in Amino Acid Mimetics and Peptidomimetics, Abell, A., Ed., JAI Press, Greenwitch, 1997, vol. 2, pp. 193-232.*
MacDonald and Aube 2001 Curr. Org. Chem. 5: 417-438.*
Kahn et al., Tetrahedron Lett. 27: 4841-4844 (1986), discloses an internal beta-turn mimetic, based upon an indolizidinone skeleton, and designed to mimic the lysine and arginine side-chain disposition of the immunosuppressing tripeptide Lys-Pro-Arg.*
Khiat et al., Conformational analysis of endothelin-1 analogs with indolizidinone amino acids incorporated at the C-terminus. Journal of Cardiovascular Pharmacology (2000), 36(5, Suppl. 1), S33-S35 (abstract; applicant (1) author).*
http://en.wikipedia.org/wiki/Prostaglandin_F2alpha (Oct. 14, 2013).*
Abramovitz, M. et al., Cloning and Expression of a cDNA for the Human Prostanoid FP Receptor, J. Biol. Chem, 269(4): 2632-2636 (1994).
Abran, D. et al., Regulation of prostanoid vasomotor effects and receptors in choroidal vessels of newborn pigs, Am. J. Physiol. (Regulatory Integrative Comp. Physiol 41): R995-R1001 (1997).
Almquist, R.G. et al., Synthesis and Biological Activity of a Ketomethylene Analogue of a Tripeptide Inhibitor of Angiotensin Converting Enzyme, J. Med. Chem, 23: 1392-1398 (1980).
Baldwin, J.M. et al., An Alpha-carbon Template for the Transmembrane Helices in the Rhodopsin Family of G-protein-coupled Receptors, J. Mol. Biol. 272: 144-164 (1997).
Berridge, M.J. et al., Changes in the levels of inositol phosphates after agonist-dependent hydrolysis of membrane phosphoinositides, Biochem. J. 212: 473-482 (1983).
Coleman, R.A. et al., VIII. International Union of Pharmacology—Classification of Prostanoid Receptors: Properties, Distribution, and Structure of the Receptors and Their Subtypes, Pharmacol. Rev. 46: 205-229 (1994).
Crankshaw, D.J. et al., Effects of Prostanoids on the Rat's Myometrium in Vitro during Pregnancy, Biology of Reproduction 46: 392-400 (1992).
Crankshaw, D.J. et al., Effects of some naturally occurring prostanoids and some cyclooxygenase inhibitors on the contractility of the human lower uterine segment in vitro, Can J Physiol Pharmacol 72: 870-874 (1994).

(Continued)

*Primary Examiner* — Maury Audet
(74) *Attorney, Agent, or Firm* — Gottlieb, Rackman & Reisman, P.C.

(57) ABSTRACT

The invention relates to compositions which are useful for inhibiting prostaglandin $F_{2\alpha}$ receptor. The compositions include, but are not limited to, linear peptides, peptide analogs, and peptidomimetics. Methods of using the compositions of the invention to treat preterm labor and dysmenorrhea are disclosed.

11 Claims, 10 Drawing Sheets

(56) References Cited

OTHER PUBLICATIONS

Findeis, M.A. et al., Nitrobenzophenone Oxime Based Resins for the Solid-Phase Synthesis of Protected Peptide Segments, J. Org. Chem. 54: 3478-3482 (1989).
Gennari, C. et al., Solid-Phase Synthesis of Peptides Containing Reverse-Turn Mimetic Bicyclic Lactams, Eur. J. Org. Chem. No. 2, pp. 379-388 (1999).
Gill, P. et al., Synthesis of Enantiopure Arylkainoids: Preparation of (2S)-Δ3-4-Phenylkainic Acid, J. Org. Chem. 60: 2658-2659 (1995).
Goetzl, E.J. et al., Specificity of expression and effects of eicosanoid mediators in normal physiology and human diseases, FASEB J. 9: 1051-1058 (1995).
Goodman, M. et al. The Synthesis and Conformational Analysis of Retro-Inverso Analogues of Biologically Active Molecules, Persepectives in Peptide Chemistry pp. 283-294 (1981).
Gosselin, F. et al., An Olefination Entry for the Synthesis of Enantiopure α,ω-Diaminodicarboxylates and Azabicyclo [X.Y.0] alkane Amino Acids, J. Org. Chem. 63: 7463-7471 (1998).
Gosselin, F. et al., Rigid Dipeptide Surrogates: Syntheses of Enantiopure Quinolizidinone and Pyrroloazepinone Amino Acids from a Common Diaminodicarboxylate Precursor, J. Org. Chem. 65: 2163-2171 (2000).
Gosselin, F. et al., Probing opiod receptor-ligand interactions by employment of indolizidin-9-one amino acid as a constrained Gly2-Gly3 surrogate in a leucine-enkephalin mimic, J. Peptide Res. 57(4): 337-344 (2001).
Griffin, B.W. et al. AL-8810: A Novel Prostaglandin F2α Analog with Selective Antagonist Effects at the Prostaglandin F2α (FP) Receptor, J. Pharmacol. Exp. Ther. 290(3): 1278-1284 (1999).
Guy, C.A. et al., Trifluoroacetic Acid Cleavage and Deprotection of Resin-Bound Peptides Following Synthesis by Fmoc Chemistry, Methods in Enzymology 289: 67-83 (1997).
Halab, L, et al., Design, Synthesis, and Conformational Analysis of Azacycloalkane Amino Acids as Conformationally Constrained Probes for Mimicry of Peptide Secondary Structures, Biopolymers 55 (2): 101-122 (2000).
Hanessian, S. et al., Design and Synthesis of Conformationally Constrained Amino Acids as Versatile Scaffolds and Peptide Mimetics, Tetrahedron 53: 12789-12854 (1997).
Hann, M.M. et al., On the Double Bond Isostere of the Peptide Bond: Preparation of an Enkephalin Analogue, Chem. Soc. Perkin Trans. I pp. 307-314 (1982).
Hebert, T.E. et al., A Peptide Derived from a β2-Adrenergic Receptor Transmembrane Domain Inhibits Both Receptor Dimerization and Activation, J. Biol. Chem. 271: 16384-16392 (1996).
Holladay, M.W. et al., Synthesis of Hydroxyethylene and Ketomethylene Dipeptide Isosteres, Tetrahedron Lett. 24(41): 4401-4404 (1983).
Hruby, V. J. Conformational Restrictions of Biologically Active Peptides Via Amino Acid Side Chain Groups, Life Sci. 31: 189-199 (1982).
Hudson, D. et al., Methionine Enkephalin and Isosteric Analogues, Int. J. Pept. Prot. Res. 14: 177-185 (1979).
James, G.L. et al., Benzodiazepine Peptidomimetics: Potent Inhibitors of Ras Farnesylation in Animal Cells, Science 260: 1937-1942 (1993).
Jennings-White, C. et al., Synthesis of Ketomethylene Analogs of Dipeptides, Tetrahedron Lett, 23(25): 2533-2534 (1982).
Kitanaka J. et al, Phloretin as an Antagonist of Prostaglandin F2α Receptor in Cultured Rat Astrocytes, J. Neurochem. 60: 704-708 (1993).
Lake, S. et al., Cloning of the rat and human prostaglandin F2α receptors and the expression of the rat prostaglandin F2α receptor, FEBS Letters 355 (3): 317-325 (1994).
Lefevre, P.G., Sugar Transport in the Red Blood Cell: Structure-Activity Relationships in Substrates and Antagonists, Pharmacol. Rev. 13: 39-70 (1961).
Li, D. et al., Inhibition of Prostaglandin Synthesis in Newborn Pigs Increases Cerebral Microvessel Prostaglandin F2α and Prostaglandin E2 Receptors, Their Second Messengers and Vasoconstrictor Response to Adult Levels, J. Pharmacol. Exp. Ther. 278(1): 370-377 (1996).
Li, D. et al., Key role for cyclooxygenase-2 in PGE2 and PGF2α receptor regulation and cerebral blood flow of the newborn, Am. J. Physiol. (Regulatory Integrative Comp. Physiol 42):. R1283-R1290 (1997).
Lofts, F.J. et al., Specific short transmembrane sequences can inhibit transformation by the mutant neu growth factor receptor in vitro and in vivo. Oncogene 8: 2813-2820 (1993).
Lombart, H. et al., Rigid Dipeptide Mimetics: Efficient Synthesis of Enantiopure Indolizidinone Amino Acids, J. Org. Chem. 61: 9437-9446 (1996).
MacDonald, M. et al., Approaches to Cyclic Peptide β-Turn Mimics, Curr. Org. Chem. 5: 417-438 (2001).
Merrifield, R.B., Solid Phase Peptide Synthesis. I. The Synthesis of a Tetrapeptide, J. Am. Chem. Soc. 85: 2149-2154 (1963).
Morley, J.S., Modulation of the action of regulatory peptides by structural modification, Trends Pharm. Sci. 463-468 (1980).
Nagai, U. et al., Bicyclic Turned Dipeptide (BTD) as a β-Turn Mimetic; its Design, Synthesis and Incorporation into Bioactive Peptides, Tetrahedron 49(17): 3577-3592 (1993).
Peri, K.G. et al., THG113: A Novel Selective FP Antagonist that Delays Preterm Labor, Seminars in Perinatology 26 (6): 389-397 (2002).
Polyak, F. et al., Rigid Dipeptide Mimics: Synthesis of Enantiopure 5- and 7-Benzyl and 5,7-Dibenzyl Indolizidinone Amino Acids via Enolization and Alkylation of δ-Oxo α,ω-Di-[N-(9-(9-phenylfluorenyl)amino]azelate Esters, J. Org. Chem. 63: 5937-5949 (1998).
Potvin, W. et al., Refractoriness of the gravid rat uterus to tocolytic and biochemical effects of atrial natriuretic peptide, Br. J. Pharmacol. 100: 341-347 (1990).
Powell, A.M. et al., Menstrual-PGF2α, PGE2 and TXA2 in Normal and Dysmenorrheic Women and Their Temporal Relationship to Dysmenorrhea, Prostaglandins 29(2): 273-289 (1985).
Rehwald, M. et al., Possible role for ligand binding of histidine 81 in the second transmembrane domain of the rat prostaglandin F2α, receptor, FEBS Letters 443(3): 357-362 (1999).
Senior, J. et al., In vitro characterization of prostanoid FP-, DP-, IP- and TP-receptors on the non-pregnant human myometrium, Br. J. Pharmacol. 107: 215-221 (1992).
Spatola, A.F. et al., Structure-Activity Relationships of Enkephalins Containing Serially Replaced Thiomethylene Amide Bond Surrogates, Life Sci. 38: 1243-1249 (1986).
Stewart, J. M., Cleavage Methods Following Boc-Based Solid-Phase Peptide Synthesis, Methods in Enzymology 289: 29-44 (1997).
Strader, C.D. et al., Structure and Function of G Protein-Coupled Receptors, Ann. Rev. Biochem. 63: 101-132 (1994).
Sugimoto, Y. et al., Failure of Parturition in Mice Lacking the Prostaglandin F Receptor, Science 277: 681-683 (1997).
Taylor, J.M. et al Peptides as Probes for G Protein Signal Transduction, Cell Signal. 6(8): 841-849 (1994).
Thorell, J.I. et al., Enzymatic Iodination of Polypeptides with 125I to High Specific Activity, Biochim. Biophys. Acta 28, 251 (3): 363-369 (1971).
Thouin, E. et al., Effective synthesis of enantiopure hydroxamates by displacement of resin-bound esters with hydroxylamine, Tetrahedron Lett. 41: 457-460 (2000).
Unger, V.M. et al., Arrangement of rhodopsin transmembrane α-helices, Nature 289: 203-206 (1997).
Varma, D.R. et al., Endothelium- and Beta-2 Adrenoceptor-Independent Relaxation of Rat Aorta by Tyramine and Certain Other Phenylethylamines, J. Pharmacol. Exp. Ther. 265(3): 1096-1104 (1993).
Wellings, D.A. et al., Methods for Solid-Phase Assembly of Peptides: [4] Standard Fmoc Protocols, Methods in Enzymology 289: 44-67 (1997).

* cited by examiner

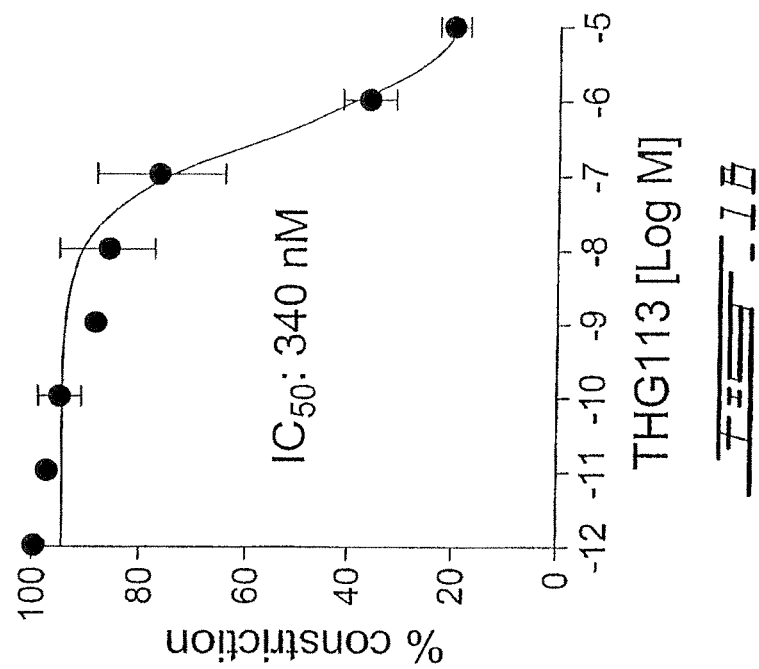
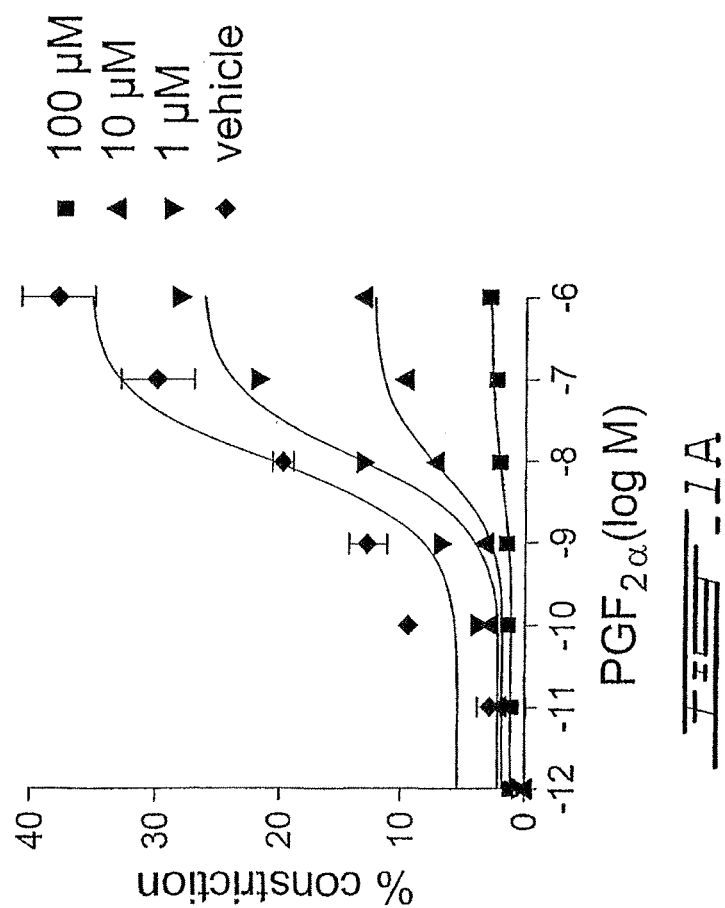
FIG. 1A
FIG. 1B

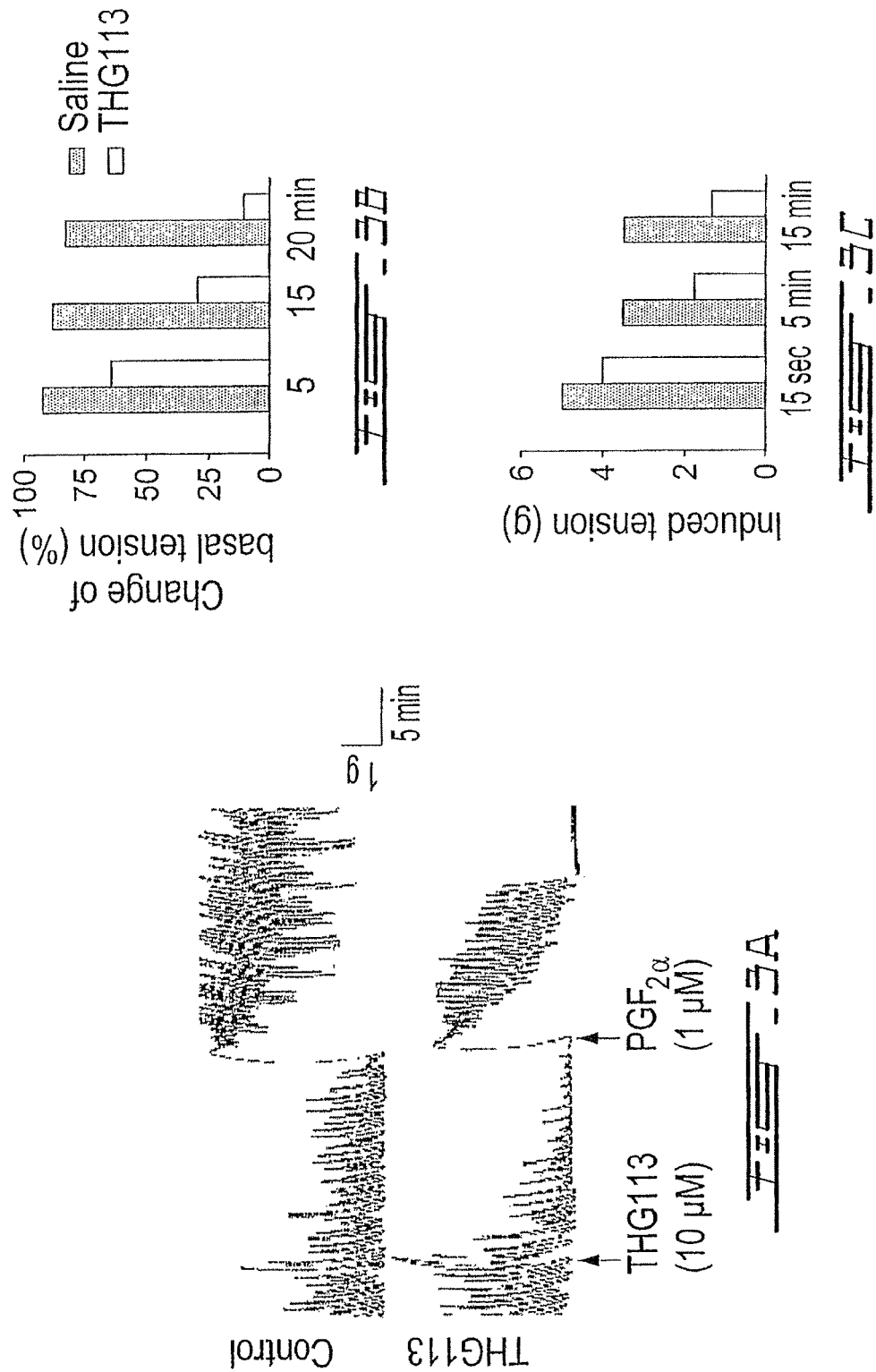

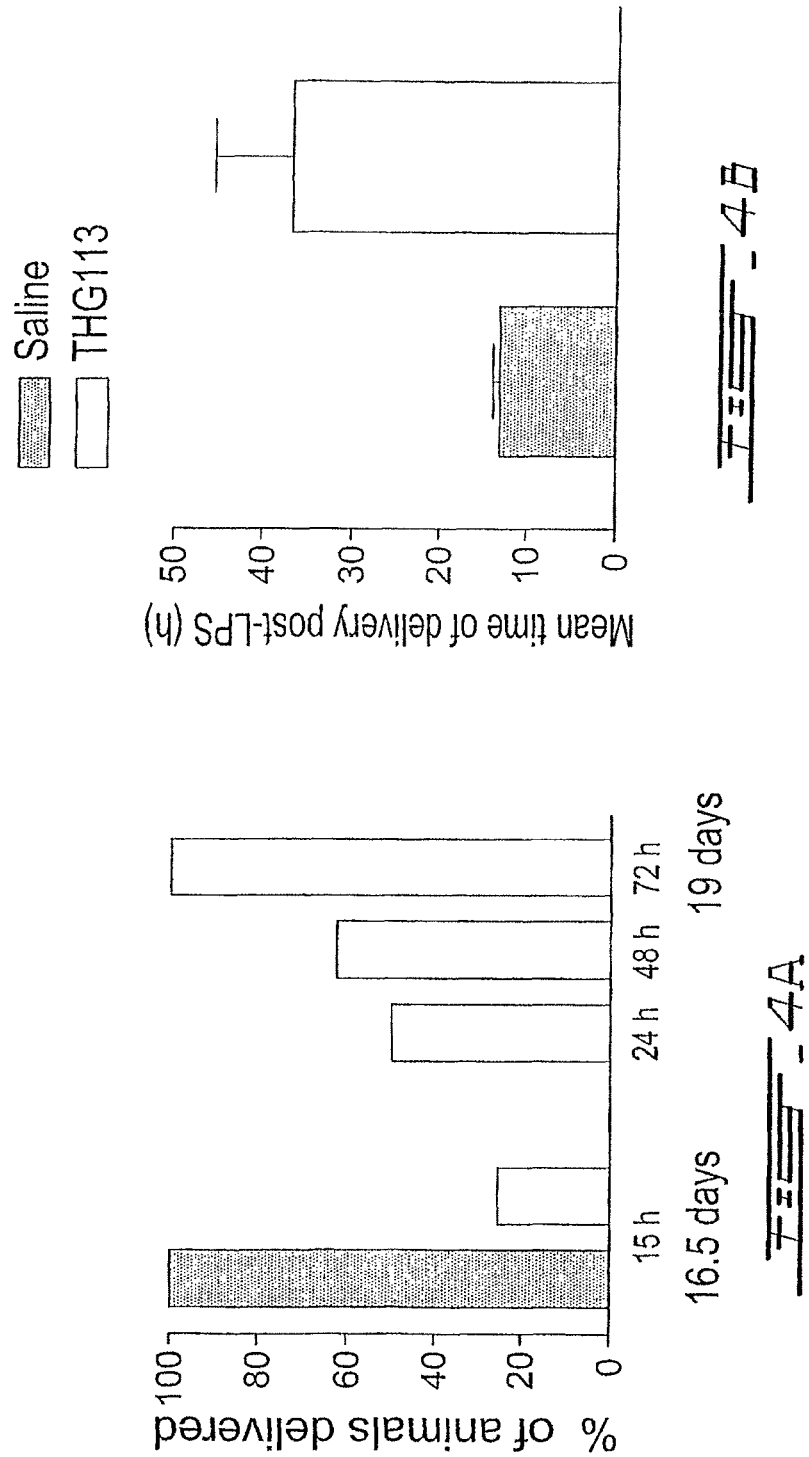

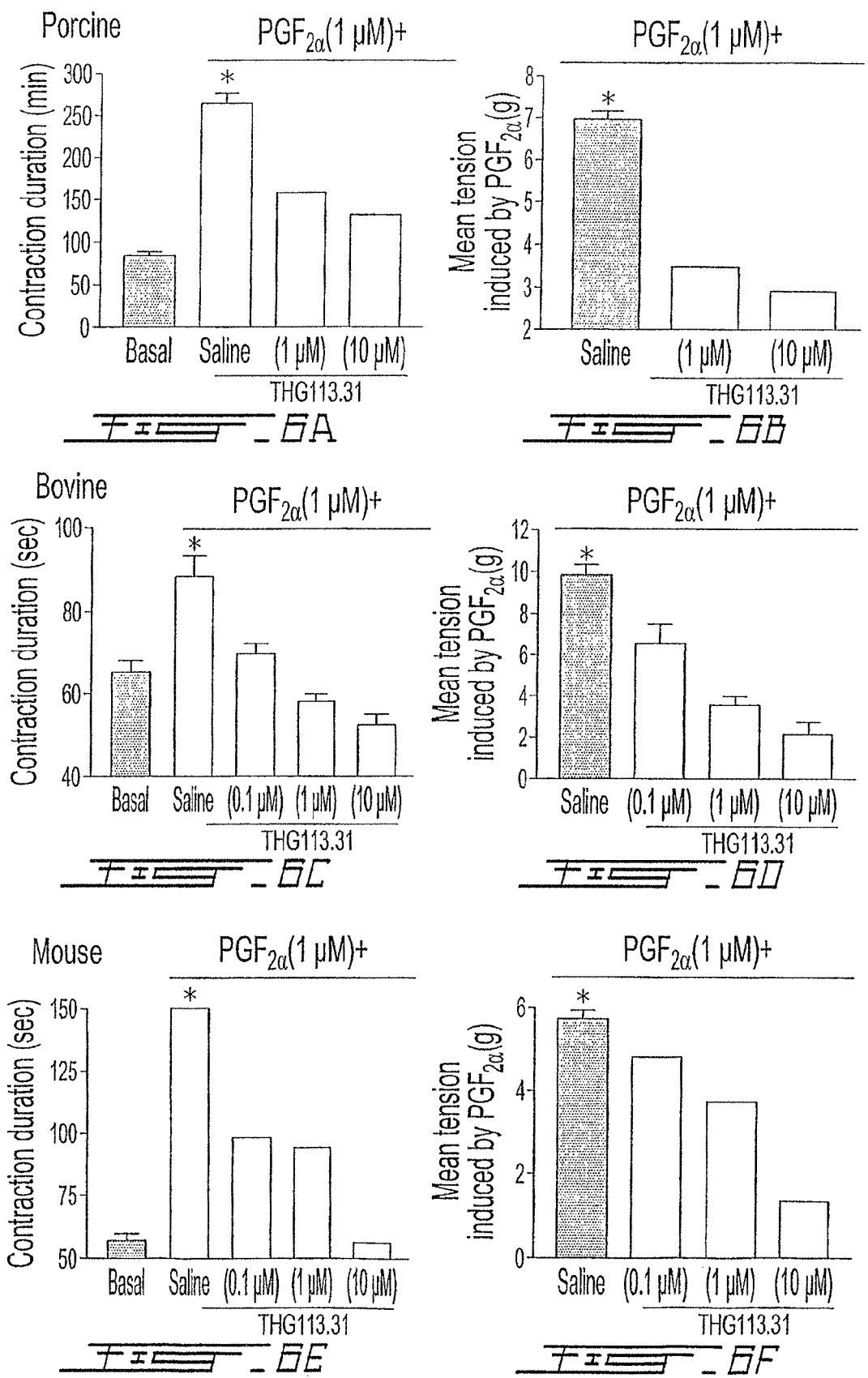

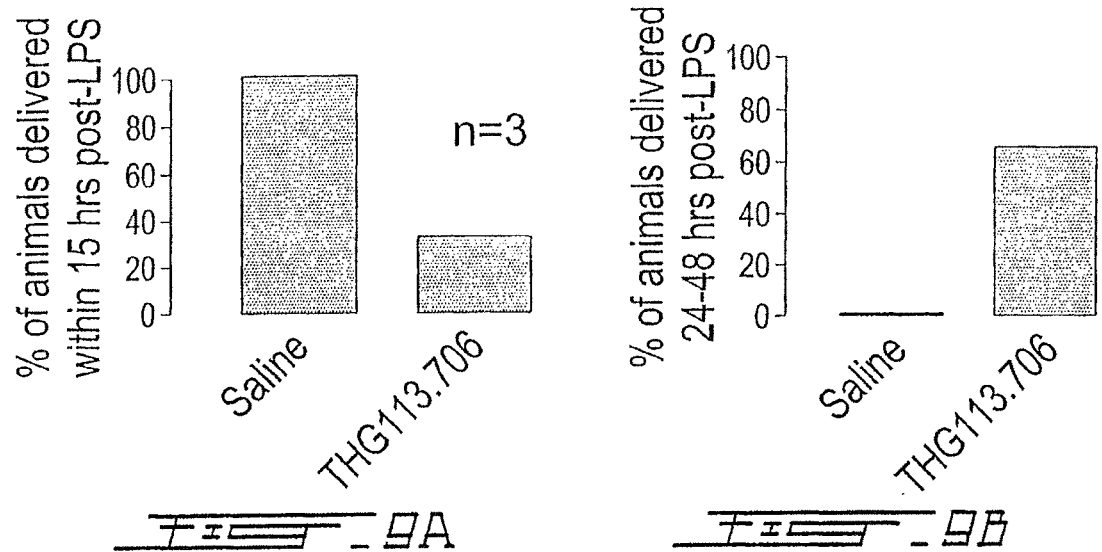
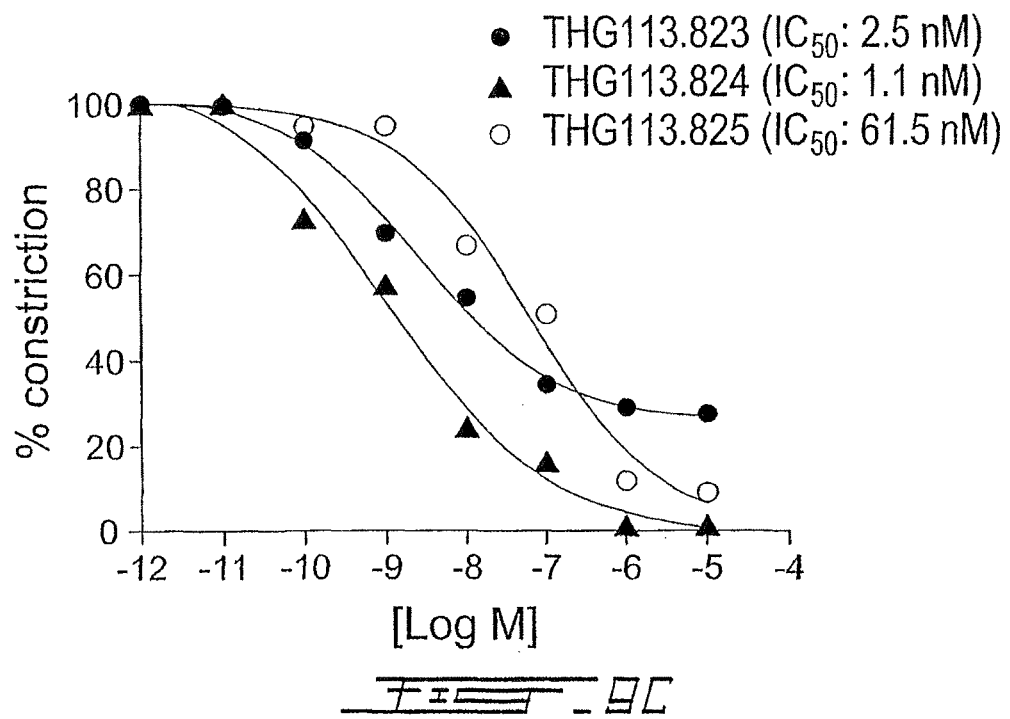

SEQUENCE LISTING

<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Ile Leu Gly His Arg Asp Tyr Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Gly His Arg Asp Tyr Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

Ile Leu Gly Ala Arg Asp Tyr Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Ile Leu Gly His Ala Asp Tyr Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Ile Leu Gly His Arg Ala Tyr Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: L-amino acid

```
<400> SEQUENCE: 6

Ile Leu Gly His Arg Ala Tyr Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: L-amino acid

<400> SEQUENCE: 7

Ile Leu Gly His Arg Asp Glu Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: L-amino acid

<400> SEQUENCE: 8

Ile Leu Gly His Arg Asp Tyr Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Ile Leu Ala His Arg Asp Tyr Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: L-amino acid

<400> SEQUENCE: 10

Ile Leu Ala His Arg Asp Tyr Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 11
```

```
Ile Leu Gly His Arg Asp Tyr Trp
1               5
```

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

```
Ile Leu Gly His Arg Asp Glu Lys
1               5
```

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13

```
Ile Leu Gly Phe Arg Asp Tyr Lys
1               5
```

<210> SEQ ID NO 14
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 14

```
Ile Leu Gly His Arg Glu Tyr Lys
1               5
```

<210> SEQ ID NO 15
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 15

```
Ile Leu Gly His Lys Asp Tyr Lys
1               5
```

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 16

```
Ile Leu Gly His Arg Asn Tyr Lys
1               5
```

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 17

```
Ile Leu Gly His Arg Asp Tyr
```

```
<210> SEQ ID NO 18
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 18

Ile Leu Pro His Arg Asp Tyr Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Ile Leu His Arg Asp Tyr Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 20

Ile Leu Gly His Gln Asp Tyr Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 21

Ile Leu Gly His Arg Ser Tyr Lys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: AMIDATION
<222> LOCATION: (7)..(7)
<223> OTHER INFORMATION: The COOH group at the terminus of the amino
      acid (Tyr) at position 7 has been replaced with a CONH2
      group

<400> SEQUENCE: 22

Ile Leu Gly His Arg Asp Tyr
1               5

<210> SEQ ID NO 23
<211> LENGTH: 8
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: AMIDATION
<222> LOCATION: (8)..(8)
<223> OTHER INFORMATION: The COOH group at the terminus of the amino
      acid (Lys) at position 8 has been replaced with a CONH2
      group

<400> SEQUENCE: 23

Ile Leu Gly His Arg Asp Tyr Lys
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 24

Ile Leu Gly Trp Arg Asp Tyr Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 25

Ile Leu Gly Tyr Arg Asp Tyr Lys
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa = D-cyclohexylalanine

<400> SEQUENCE: 26

Ile Leu Gly Xaa Arg Asp Tyr Lys
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa = cyclohexylalanine

<400> SEQUENCE: 27

Ile Leu Gly Xaa Gln Asp Tyr Lys
1               5

<210> SEQ ID NO 28
<211> LENGTH: 8
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa = D-cyclohexylalanine

<400> SEQUENCE: 28

Ile Leu Gly Xaa Arg Asn Tyr Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 29

Lys Tyr Asp Arg His Gly Leu Leu
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(7)
<223> OTHER INFORMATION: Xaa = L-pyridylalanine

<400> SEQUENCE: 30

Ile Leu Gly His Xaa Xaa Xaa Gln Asp Tyr Lys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(8)
<223> OTHER INFORMATION: Xaa = L-pyridylalanine

<400> SEQUENCE: 31

Ile Leu Gly His Xaa Xaa Xaa Xaa Asp Tyr Lys
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa = citrulline

<400> SEQUENCE: 32

Ile Leu Gly His Xaa Asp Tyr Lys
1               5
```

PEPTIDES AND PEPTIDOMIMETICS USEFUL FOR INHIBITING THE ACTIVITY OF PROSTAGLANDIN $F_{2\alpha}$ RECEPTOR This application is a continuation of U.S. Ser. No. 10/517,687 filed Dec. 10, 2004 now U.S. Pat. No. 7,521,530, the contents of which is incorporated herein by reference.

FIELD OF THE INVENTION

The subject of the present invention relates to mimetics of a peptide inhibitor of prostaglandin $F_{2\alpha}$ (FP) receptor. Furthermore, the invention also relates to methods of treating premature labor and dysmenorrhea using pharmaceutical compositions containing the said peptidomimetic inhibitors of FP receptor.

BACKGROUND

Prostaglandins are derived from the oxygenation of arachidonic acid by prostaglandin syntheses. Prostaglandins mediate a wide variety of physiological actions, such as vasomotricity, sleep/wake cycle, intestinal secretion, lipolysis, glomelular filtration, mast cell degranulation, neurotransmission, platelet aggregation, leuteolysis, myometrial contraction and labor, inflammation and arthritis, patent ductus arteriosus, cell growth and differentiation (Coleman, R. A., Smith, W. L., and Narumiya, S. 1994. Pharmacol. Rev. 46: 205-229; Goetzl, E. J., An, S, and Smith, W. L. 1995. FASEB J. 9:1051-10585). Prostanoids mediate their actions through binding to distinct receptors which belong to the super family of rhodopsin-like seven transmembrane helical receptors. These receptors are coupled to heterotrimeric G-proteins comprised of α, β and γ subunits which, upon activation, elicit alterations in cell calcium, initiate phosphoinositide hydrolysis or promotion or repression of cyclic adenosine monophosphate synthesis (Strader C. D. et al., 1994 Ann. Rev. Biochem. 63: 101-132).

Of the five pharmacologically distinct prostanoid receptors for $PGE_2$, $PGI_2$, $PGD_2$, $PGF_{2\alpha}$, and $TxA_2$ and their many isoforms, the receptor for $PGF_{2\alpha}$, also called FP receptor, shows limited tissue distribution, is predominantly expressed in corpora leutea, uterine myometrium, trabecular meshwork of the eye, and to a lesser extent in vascular smooth muscle. Initiation of labor is marked by a tremendous rise in $PCF_{2\alpha}$ levels and increased uterine contractility. The wide spread use of $PGF_{2\alpha}$ analogues to induce labor in veterinary industry points to the primary role of $PGF_{2\alpha}$ and its receptor in parturition. This is underscored by the fact that mice lacking the FP receptor fail to undergo labor (Sugimoto et al., Science, 277: 81-83, 1997). In the face of escalating costs incurred as a result of premature births and associated complications to the neonate, such as intraventricular hemorrhage, bronchopulmonary displasia and periventricular leukomalacia leading to cerebral palsy, prolongation of gestation by arresting premature labor is an effective preventive therapy. The relative success of nonsteroidal anti-inflammatory drugs as a short term therapy toward prevention of premature labor is based on their inhibitory actions upon the synthesis of prostaglandins, particularly $PGE_2$ and $PGF_{2\alpha}$. However, inhibition of the former is associated with serious complications to the fetus such as the closure of ductus arteriosus, renal failure and pulmonary hypertension. Hence there is a therapeutic need for finding antagonists of FP receptor to treat premature labor.

At another level, $PGF_{2\alpha}$ has been attributed to a major role in dysmenorrhea, a condition which afflicts 5%-7% of pre-menopausal women. A pre-menstrual increase in $PGF_{2\alpha}$ levels resulting in myometrial spasms underlies the pathogenesis of this disorder. Lack of effective antagonists of FP receptor for extended therapy hampered the advances in preventing premature labor and associated sequelae, and the provision of such antagonists is the subject of this application.

Human FP receptor is a 45 kDa integral membrane glycoprotein, consisting of 359 amino acids and shares only 47% sequence identity with $EP_1$ receptor, and to a lesser extent with other prostanoid receptors (Abramovitz et al. 1994. J. Biol. Chem. 269: 2632-2636). Binding of $PGF_{2\alpha}$ to FP receptor is followed by the activation of the $G_{\alpha\beta\gamma}$ complex, increased GTP binding by the $G_\alpha$ subunit, stimulation of phospholipase Cβ activity, release of inositol phosphates, increased intracellular calcium and subsequent signal transduction phenomena ultimately leading to smooth muscle contraction (Coleman, R. A. et al. 1994. Pharmacol. Rev. 46: 205-229). Since the natural ligand, $PGF_{2\alpha}$ and the ligand-based compounds have cross-reactivity with other prostanoid receptors and to date, no effective and selective antagonists of FP receptor have been disclosed, it is of immediate therapeutic relevance in preterm labor and dysmenorrhea to provide FP antagonists, as is done in this present invention.

Modification of the natural ligand of FP receptor, $PGE_{2\alpha}$, yielded potent and selective agonists of the receptor, however selective and potent antagonists were not disclosed by these approaches. Two compounds, Phloretin (Kitanaka J et al 1993 J Neurochem 60: 704-708) and AL8810 (Griffin B W et al 1999. J. Pharmacol. Exp. Ther. 290 (3): 1278-1284) have been shown to have antagonistic activity to FP receptor. Phloretin, also shown to have antagonistic effects on glucose transport (Lefevre P G 1961. Pharmacol Rev 13: 39-70) is a weak antagonist of FP receptor ($IC_{50}$ 20 μM) and nonselective with respect to $PGE_2$. AL8810, an 11-fluoro 15(2-indanyl) derivative of $PGF_{2\alpha}$, is shown to be a weak partial agonist of FP receptor, even though it is found to selectively antagonize FP receptor in the presence of a fluprostenol, a full agonist of FP receptor (Griffin B W et al 1999. J. Pharmacol. Exp. Ther. 290 (3): 1278-1284).

Hence there is need to provide highly selective and potent antagonists to FP receptor with a view to develop therapeutic formulations to arrest premature labor and dysmenorrhea. Most importantly, embodiments of the present invention contain inhibitors of FP receptor, and demonstration of the inhibitory action of said peptides and their peptidomimetics on the biological activity of FP receptor. Exemplary embodiments include the utility of the peptide and peptidomimetic inhibitors for reducing the intensity of uterine contraction, said contraction being a central mechanism involved in the initiation and progression of labor as well as menstrual pain.

SUMMARY OF THE INVENTION

The invention relates to a peptide, wherein the peptide is characterized by Formula I $$Y\text{-}AA_1\text{-}AA_2\text{-}AA_3\text{-}AA_4\text{-}AA_5\text{-}AA_6\text{-}AA_7\text{-}AA_8\text{-}Z \qquad \text{Formula I}$$

wherein:

Y is attached to the amino-terminus of the peptide and is selected from the group consisting of a hydrogen atom, an acetyl group, a benzoyl group, an acyl group (R—CO—), wherein R is a hydrophobic moiety, or an aroyl group (Ar—CO—), wherein Ar is an aryl group;

Each of $AA_1$ and $AA_2$ are independently selected from the group consisting of no residue, isoleucine (Ile), leucine (Leu), and related alpha-amino acids possessing hydrophobic side-chains;

$AA_3$ is selected from the group consisting of no residue, glycine (Gly), alanine (Ala) and proline (Pro);

$AA_4$ is selected from the group consisting of histidine (His), phenylalanine (Phe), tyrosine (Tyr), tryptophan (Trp) and related alpha-amino acids possessing hydrophobic side-chains;

$AA_5$ is selected from the group consisting of arginine (Arg), ornithine (Orn), lysine (Lys), citruline, 2-, 3-, and 4-pyridylalanine, and arginine surrogates;

$AA_6$ is selected from the group consisting of aspartic acid (Asp), asparagine (Asn), glutamic acid (Glu), glutamine (Gln), serine (Ser), 3-amino-5-phenylpentanoic acid and Phe;

$AA_7$ is selected from the group consisting of no residue, Tyr, Phe, and related alpha-amino acids possessing hydrophobic side-chains, aromatic and arylalkyl amines, and aliphatic amines;

$AA_8$ is selected from the group consisting of no residue, Lys, Leu, Tyr, alpha-amino acids possessing hydrophobic side-chains, and aromatic and aliphatic amines;

Z is attached to the carboxy-terminus of said peptide and is selected from the group consisting of, a hydroxyl group, $NH_2$, and aromatic and aliphatic amines; and functional derivatives thereof.

This invention also includes optical isomers, diastereomers and enantiomers of the formulae above, and pharmaceutically-acceptable salts, biohydrolyzable amides, esters, and imides thereof.

In a preferred embodiment, the acyl group in the definition of Y is selected from the group consisting of benzoyl, acetyl, tert-butyl acetyl, para-phenyl benzoyl, trifluoroacetyl, cyclohexylcarbonyl and phenylacetyl.

In a preferred embodiment, the hydrophobic moiety in the definition of Y is selected from the group consisting of a substituted or unsubstituted alkyl, a substituted or non-substituted cycloalkyl, a phenylmethyl, and a saturated or unsaturated hydrocarbon chain.

In a preferred embodiment, the substituted or unsubstituted alkyl is a saturated hydrocarbon chain having from 1 to 18 C atoms.

In a preferred embodiment, the substituted or unsubstituted alkyl is a saturated hydrocarbon chain having from 1 to 12 C atoms.

In a preferred embodiment, the substituted or unsubstituted alkyl is a saturated hydrocarbon chain having from 1 to 6 C atoms.

In a preferred embodiment, the substituted or unsubstituted alkyl is a saturated hydrocarbon chain having from 1 to 4 C atoms.

In a preferred embodiment, the substituted or unsubstituted alkyl is a linear hydrocarbon chain.

In a preferred embodiment, the substituted or unsubstituted alkyl is a branched hydrocarbon chain.

In a preferred embodiment, the branched hydrocarbon chain has one or two branches.

In a preferred embodiment, the branched hydrocarbon chain has one branch.

In a preferred embodiment, the substituted or unsubstituted alkyl is an unsaturated hydrocarbon chain having 3 to 18 C atoms.

In a preferred embodiment, the unsaturated hydrocarbon chain has at least one double bond and/or at least one triple bond.

In a preferred embodiment, the unsaturated hydrocarbon chain has two double bonds.

In a preferred embodiment, the unsaturated hydrocarbon chain has one double bond.

In a preferred embodiment, the unsaturated hydrocarbon chain has one triple bond.

In a preferred embodiment, the substituted alkyl is selected from the group consisting of a mono-, a di- and a tri-substituted alkyl.

In a preferred embodiment, the substituted alkyl is substituted with from 1 to 4 substituents.

In a preferred embodiment, the substituent is selected from the group consisting of halo, haloalkyl, hydroxy, aryl, heterocyclyl and heteroaryl.

In a preferred embodiment, the aryl is selected from the group consisting of phenyl, tolyl, alkyloxyphenyl, alkyloxycarbonylphenyl, and halophenyl.

In a preferred embodiment, the substituted or unsubstituted cycloalkyl is a saturated ring of from 3 to 8 C atoms.

In a preferred embodiment, the substituted or unsubstituted cycloalkyl is selected from the group consisting of cyclopentyl and cyclohexyl.

In a preferred embodiment, the substituted cycloalkyl is selected from the group consisting of mono- and di-substituted cycloalkyl.

In a preferred embodiment, the substituted cycloalkyl has substituents selected from the group consisting of halo, haloalkyl, hydroxy, aryl, heterocyclyl and heteroaryl.

In a preferred embodiment, the aryl is selected from the group consisting of phenyl, tolyl, alkoxyphenyl, alkoxycarbonylphenyl and halophenyl.

In a preferred embodiment, the saturated or unsaturated hydrocarbon chain is selected from the group consisting of a linear saturated or unsaturated alkyl group, an alkenyl group, and branched saturated or unsaturated alkyl group.

In a preferred embodiment, the linear saturated alkyl group has from 1 to 18 C atoms.

In a preferred embodiment, the linear saturated alkyl group has from 1 to 12 C atoms.

In a preferred embodiment, the linear saturated alkyl group has from 1 to 6 C atoms.

In a preferred embodiment, the linear saturated alkyl group has from 1 to 4 C atoms.

In a preferred embodiment, the alkenyl group has 3 to 8 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, in the definition of $AA_4$, the hydrophobic side-chain is selected from the group consisting of cyclohexylalanine and heterocyclic side-chains.

In a preferred embodiment, the heterocyclic side-chain is a pyridylalanine group.

In a preferred embodiment, in the definition of $AA_7$, $AA_8$ and Z, the aromatic amine is selected from the group consisting of phenylmethylamine, phenylethylamine, phenylproplyamine, and an amine comprising a saturated or unsaturated hydrocarbon chain.

In a preferred embodiment, in the definition of $AA_7$, $AA_8$ and Z, the aliphatic amine is selected from the group consisting of amines comprising a saturated or unsaturated hydrocarbon chain.

In a preferred embodiment, the amine comprising a saturated or unsaturated hydrocarbon chain is a primary amine.

In a preferred embodiment, the saturated or unsaturated hydrocarbon chain is selected from the group consisting of a linear saturated or unsaturated alkyl group, an alkenyl group, and a branched saturated or unsaturated alkyl group.

In a preferred embodiment, the linear saturated alkyl group has from 1 to 18 carbon atoms and the linear unsaturated alkyl group has 3 to 18 C atoms.

In a preferred embodiment, the linear saturated alkyl group has from 1 to 12 carbon atoms and the linear unsaturated alkyl group has 3 to 12 C atoms.

In a preferred embodiment, the linear saturated alkyl group has from 1 to 6 carbon atoms and the linear unsaturated alkyl group has 3 to 6 C atoms.

In a preferred embodiment, the linear saturated alkyl group has from 1 to 4 carbon atoms and the linear unsaturated alkyl group has 3 to 4 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, in the definitions of $AA_1$ to $AA_8$, the amino acids are D- or L-amino acids.

In a preferred embodiment, in the definition of $AA_7$, $AA_8$ and Z, the aromatic amine is a primary aromatic amine.

In a preferred embodiment, in the definition of $AA_7$, the primary arylalkyl amine has a ring of from 6 to 10 C atoms.

In a preferred embodiment, in the primary arylalkyl amine, the aryl is selected from the group consisting of phenyl, tolyl, alkoxyphenyl, alkoxycarbonylphenyl and halophenyl.

In a preferred embodiment, the primary aromatic amine has a ring of from 6 to 10 C atoms.

In a preferred embodiment, in the definition of $AA_7$, $AA_8$ and Z the aliphatic amine is a primary aliphatic amine.

In a preferred embodiment, the primary aliphatic amine has from 1 to 18 C atoms.

In a preferred embodiment, the peptide is selected from the group consisting of SEQ ID NO 1-4, 6, 8-11, 13-32, and functional derivatives thereof.

In a preferred embodiment, the peptide and functional derivatives thereof substantially inhibit FP receptor.

In a preferred embodiment, the FP receptor is from a mammal.

In a preferred embodiment, the mammal is a human.

In a preferred embodiment, the inhibition of FP receptor is measured according to porcine retinal microvascular contraction to prostaglandin $F_{2\alpha}$, wherein the inhibition is at least 50% of that produced by the ligand in the absence of the peptide.

In a preferred embodiment, the peptide has an inhibition of the FP receptor measured according to porcine retinal microvascular contraction to prostaglandin $F_{2\alpha}$, wherein the inhibition is at least 50% of that produced by the ligand in the absence of the peptide.

The invention also relates to a pharmaceutical composition comprising a therapeutically effective amount of at, least one peptide of SEQ ID NO 1-4, 6, 8-11, 13-32, and functional derivatives thereof, in association with a pharmaceutically acceptable carrier.

In a preferred embodiment, the therapeutically effective amount of the peptide is 0.1-100 mg/Kg body weight.

In a preferred embodiment, the peptide is used alone or in combination with a pharmaceutically acceptable carrier, to inhibit EP receptor.

In a preferred embodiment, the pharmaceutical composition is used for the preparation of a medicament to arrest preterm labor.

In a preferred embodiment, the pharmaceutical composition is used for the preparation of a medicament for the treatment of dysmenorrhea.

The invention also relates to a method of arresting preterm labor comprising administering to an individual a therapeutically effective amount of pharmaceutical composition comprising at least one peptide of SEQ ID NO 1-4, 6, 8-11, 13-32, and functional derivatives thereof, in association with a pharmaceutically acceptable carrier.

The invention also relates to a method of treating dysmenorrhea comprising administering to an individual a therapeutically effective amount at least one peptide of SEQ ID NO 1-4, 6, 8-11, 13-32, and functional derivatives thereof, in association with a pharmaceutically acceptable carrier.

The invention also relates to a peptidomimetic characterized by Formula II:

$$Y\text{-BTM-}AA_1\text{-}AA_2\text{-}AA_3\text{-}Z \qquad \text{Formula II}$$

wherein:

Y is attached to the amino-terminus of the peptide and is selected from the group consisting of a hydrogen atom, an acyl group (R—CO—), wherein R is a hydrophobic moiety, or an aroyl group (Ar—CO—), wherein Ar is an aryl group;

BTM (beta turn mimetic) is a dipeptide surrogate;

$AA_1$ is selected from the group consisting of Arg, Orn, Lys, citruline, 2-, 3-, and 4-pyridylalanine, and arginine surrogates;

$AA_2$ is selected from the group consisting of Asp, Asn, Glu, Gln, Ser, 3-amino-5-phenylpentanoic acid and Phe;

$AA_3$ is selected from the group consisting of no residue, Tyr, Phe, and related alpha-amino acids possessing hydrophobic side-chains, and aromatic amines, aliphatic amines and primary arylalkyl amines;

Z is selected from the group consisting of no residue, a hydroxyl group, $NH_2$, and aromatic, heteroaromatic and aliphatic amines; and functional derivatives thereof.

In a preferred embodiment, the acyl group in the definition of Y is selected from the group consisting of benzoyl, acetyl, tert-butyl acetyl, para-phenyl benzoyl, trifluoroacetyl, cyclohexylcarbonyl and phenylacetyl.

In a preferred embodiment, the hydrophobic moiety in the definition of Y is selected from the group consisting of a substituted or non-substituted alkyl, a substituted or non-substituted cycloalkyl, a phenylmethyl, and a saturated or unsaturated hydrocarbon chain.

In a preferred embodiment, the substituted or unsubstituted alkyl is a saturated hydrocarbon chain having from 1 to 18 C atoms.

In a preferred embodiment, the substituted or unsubstituted alkyl is a saturated hydrocarbon chain having from 1 to 12 C atoms.

In a preferred embodiment, the substituted or unsubstituted alkyl is a saturated hydrocarbon chain having from 1 to 6 C atoms.

In a preferred embodiment, the substituted or unsubstituted alkyl is a saturated hydrocarbon chain having from 1 to 4 C atoms.

In a preferred embodiment, the substituted or unsubstituted alkyl is a linear hydrocarbon chain.

In a preferred embodiment, the substituted or unsubstituted alkyl is a branched hydrocarbon chain.

In a preferred embodiment, the branched hydrocarbon chain has one or two branches.

In a preferred embodiment, the branched hydrocarbon chain has one branch.

In a preferred embodiment, the substituted or unsubstituted alkyl is an unsaturated hydrocarbon chain having from 3 to 18 C atoms.

In a preferred embodiment, the unsaturated hydrocarbon chain has at least one double bond and/or at least one triple bond.

In a preferred embodiment, the unsaturated hydrocarbon chain has two double bonds.

In a preferred embodiment, the unsaturated hydrocarbon chain has one double bond.

In a preferred embodiment, the unsaturated hydrocarbon chain has one triple bond.

In a preferred embodiment, the substituted alkyl is selected from the group consisting of a mono-, a di-, and a tri-substituted alkyl.

In a preferred embodiment, the substituted alkyl is substituted with from 1 to 4 substituents.

In a preferred embodiment, the substituent is selected from the group consisting of halo, haloalkyl, hydroxy, aryl, heterocyclyl and heteroaryl.

In a preferred embodiment, the aryl is selected from the group consisting of phenyl, tolyl, alkyloxyphenyl, alkyloxycarbonylphenyl, and halophenyl.

In a preferred embodiment, the substituted or unsubstituted cycloalkyl is a saturated ring of from 3 to 8 C atoms.

In a preferred embodiment, the substituted or unsubstituted cycloalkyl is selected from the group consisting of cyclopentyl and cyclohexyl.

In a preferred embodiment, the substituted cycloalkyl is selected from the group consisting of mono- and di-substituted cycloalkyl.

In a preferred embodiment, the substituted cycloalkyl has substituents selected from the group consisting of halo, haloalkyl, hydroxy, aryl, heterocyclyl and heteroaryl.

In a preferred embodiment, the aryl is selected from the group consisting of phenyl, tolyl, alkoxyphenyl, alkoxycarbonylphenyl and halophenyl.

In a preferred embodiment, the saturated or unsaturated hydrocarbon chain is selected from the group consisting of a linear saturated or unsaturated alkyl group, an alkenyl group, and a branched saturated or unsaturated alkyl group.

In a preferred embodiment, the linear saturated alkyl group has from 1 to 18 carbon atoms.

In a preferred embodiment, the linear saturated alkyl group has from 1 to 12 carbon atoms.

In a preferred embodiment, the linear saturated alkyl group has from 1 to 6 carbon atoms.

In a preferred embodiment, the linear saturated alkyl group has from 1 to 4 carbon atoms.

In a preferred embodiment, the alkenyl group has 3 to 8 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond, and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, in the definition of $AA_3$ and Z, the aliphatic amine is selected from the group consisting of amines comprising a saturated or unsaturated hydrocarbon chain.

In a preferred embodiment, the amine comprising a saturated or unsaturated hydrocarbon chain is a primary amine.

In a preferred embodiment, the saturated or unsaturated hydrocarbon chain is selected from the group consisting of a linear saturated or unsaturated alkyl group, an alkenyl group, and a branched saturated or unsaturated alkyl group.

In a preferred embodiment, the linear saturated alkyl group has from 1 to 18 carbon atoms and the linear unsaturated alkyl group has 3 to 18 C atoms.

In a preferred embodiment, the linear saturated alkyl group has from 1 to 12 carbon atoms and the linear unsaturated alkyl group has 3 to 12 C atoms.

In a preferred embodiment, the linear saturated alkyl group has from 1 to 6 carbon atoms and the linear unsaturated alkyl group has 3 to 6 C atoms.

In a preferred embodiment, the linear saturated alkyl group has from 1 to 4 carbon atoms and the linear unsaturated alkyl group has 3 to 4 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, the dipeptide surrogate is selected from the group consisting of indolizidinone amino acids, 5- and 7-alkyl-branched indolizidinone amino acids, quinolizidinone amino acids, pyrroloazepinone amino acids, azabicyclo[X.Y.0]alkanone amino acids, heterocyclic and carbocyclic moieties, mimics of beta-turn structure and lactam analogs.

In a preferred embodiment, in the definitions of $AA_1$ to $AA_3$, the amino acids are D- or L-amino acids.

In a preferred embodiment, in the definition of $AA_3$ and Z, the aromatic amine is a primary aromatic amine.

In a preferred embodiment, in the definition of $AA_3$, the primary arylalkyl has a ring of from 6 to 10 C atoms.

In a preferred embodiment, in the primary arylalkyl, the aryl is selected from the group consisting of phenyl, tolyl, alkoxyphenyl, alkoxycarbonylphenyl and halophenyl.

In a preferred embodiment, the primary aromatic amine has a ring of from 6 to 10 C atoms.

In a preferred embodiment, in the definition of $AA_3$ and Z the aliphatic amine is a primary aliphatic amine.

In a preferred embodiment, the primary aliphatic amine has from 1 to 10 C atoms.

In a preferred embodiment, the peptidomimetic is selected from the group consisting of compounds numbered 33-52 as shown in Table 5, and functional derivatives thereof.

In a preferred embodiment, the peptidomimetic and functional derivatives thereof substantially inhibit FP receptor.

In a preferred embodiment, the FP receptor is from a mammal.

In a preferred embodiment, the mammal is a human.

In a preferred embodiment, the inhibition of FP receptor is measured according to porcine retinal microvascular contraction to prostaglandin $F_{2\alpha}$, wherein the inhibition is at least 50% of that produced by the ligand in the absence of the peptidomimetic.

In a preferred embodiment, the peptidomimetic has an inhibition of the FP receptor measured according to porcine retinal microvascular contraction to prostaglandin $F_{2\alpha}$, wherein the inhibition is at least 50% of that produced by the ligand in the absence of the peptidomimetic.

The invention also relates to a pharmaceutical composition comprising a therapeutically effective amount of at least one compound numbered 33-52 as shown in Table 5, and functional derivatives thereof, in association with a pharmaceutically acceptable carrier.

In a preferred embodiment, the therapeutically effective amount of the peptidomimetic is 0.1-100 mg/Kg body weight.

In a preferred embodiment, the peptidomimetic is used alone or in combination with a pharmaceutically acceptable carrier, to inhibit FP receptor.

In a preferred embodiment, the pharmaceutical composition is used for the preparation of a medicament to arrest preterm labor.

In a preferred embodiment, the pharmaceutical composition is used for the preparation of a medicament for the treatment of dysmenorrhea.

The invention also relates to a method of arresting preterm labor comprising administering to an individual a therapeutically effective amount of pharmaceutical composition comprising at least one compound numbered 33-52 as shown in Table 5, and functional derivatives thereof, in association with a pharmaceutically acceptable carrier.

The invention also relates to a method of treating dysmenorrhea comprising administering to an individual a therapeutically effective amount of at least one compound numbered 33-52 as shown in Table 5, and functional derivatives thereof, in association with a pharmaceutically acceptable carrier.

The invention also relates to a method of arresting uterine contractions associated with labor with a view to prolong gestation. Furthermore, the method comprises administering to an individual a pharmaceutical composition comprising a FP receptor antagonist of the present invention.

The invention also relates to a method of arresting uterine spasms associated with dysmenorrhea in which the individual diagnosed with dysmenorrhea is administered a pharmaceutical composition comprising a FP receptor antagonist of the present invention.

For the purpose of the present invention the following terms are defined below.

The term "Acyl" is intended to mean a group composed of a carbonyl plus an alkyl, heteroalkyl, a heterocyclic apliphatic ring, a heteroaromatic ring, or an aromatic ring which is suitable for acylating a nitrogen atom to form an amide, carbamate, urea, amidine or guanidine, or an oxygen atom to form an ester group. Preferred acyl groups include benzoyl, acetyl, tert-butyl acetyl, para-phenyl benzoyl, trifluoroacetyl, cyclohexylcarbonyl and phenylacetyl.

The term "alkenyl" is intended to mean a straight or branched chain radical containing from 3 to 7 carbon atoms and at least one carbon to carbon double bond. Preferred alkenyl groups include, propenyl, butenyl and pentenyl.

The term "Alkyl" is intended to mean a saturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl chains have one or two branches, preferably one branch. Preferred alkyl chains are saturated. Unsaturated alkyl chains have one or more double bonds and/or one or more triple bonds. Preferred unsaturated alkyl chains have one or two double bonds or one triple bond, more preferably one double bond. Alkyl chains may be unsubstituted or substituted with from 1 to 4 substituents. Preferred alkyl chains are unsubstituted. Preferred substituted alkyl chains are mono-, di-, or trisubstituted. Preferred alkyl chain substituents include halo, haloalkyl, hydroxy, aryl (including, but not limited to phenyl, tolyl, alkyloxphenyl, alkyloxycarbonylphenyl, and halophenyl), heterocyclyl, and heteroaryl.

The term "Cycloalkyl" is intended to mean a saturated ring of 3 to 8 carbon atoms with cyclopentyl and cyclohexyl being most preferred. Cycloalkyl rings may be unsubstituted or substituted. Substituted cycloalkyl rings are mono- or di-substituted. Preferred cycloalkyl ring substituents include halo, haloalkyl, hydroxy, aryl (including, but not limited to, phenyl, tolyl, alkoxyphenyl, alkoxycarbonyl, phenyl and halophenyl), heterocyclyl and heteroaryl.

The term "Aromatic ring" is intended to mean an aromatic hydrocarbon ring system. Aromatic rings are monocyclic or fused bicyclic ring systems. Monocyclic aromatic rings contain from 5 to 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to 4 substituents on the ring. Preferred aromatic ring substituents include: halo, cyano, alkyl, heteroalkyl, haloalkyl, phenyl, phenoxy or any combination thereof. More preferred substituents include halo and haloalkyl. Preferred aromatic rings include naphthyl and phenyl.

The term "Aryl" is intended to mean a radical derived from an "aromatic ring" by elimination of one hydrogen that is bonded to said aromatic ring.

The term "Heteroalkyl" is intended to mean a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, and more preferably still 1 to 4. Heteroalkyl chains may be straight or branched. Preferred branched heteroalkyl chains have one or two branches, preferably one branch. Preferred heteroalkyl chains are saturated. Unsaturated heteroalkyl chains have one or more double bonds and/or one or more triple bonds. Preferred unsaturated heteroalkyl chains have one or two double bonds or one triple bond, more preferably one double bond. Heteroalkyl chains may be unsubstituted or substituted with from 1 to about 4 substituents. Preferred heteroalkyl chains are unsubstituted. Preferred heteroalkyl substituents include halo, hydroxy, aryl (including, but not limited to phenyl, tolyl, alkyloxyphenyl, alkyloxycarbonylphenyl, halophenyl), heterocyclyl, and heteroaryl. As an illustration, alkyl chains substituted with the following substituents in the main chain, are heteroalkyl: alkoxy (including, but not limited to methoxy, ethoxy, propoxy, butoxy, pentoxy), aryloxy (including, but not limited to phenoxy, chlorophenoxy, tolyloxy, methoxyphenoxy, benzyloxy, alkyloxycarbonylphenoxy, acyloxyphenoxy), acyloxy (including, but not limited to propionyloxy, benzoyloxy, acetoxy), carbamoyloxy, carboxy, mercapto, alkylthio, acylthio, arylthio (including, but not limited to phenylthio, chlorophenylthio, alkylphenylthio, alkoxyphenylthio, benzylthio, alkyloxycarbonylphenylthio), or amino (including, but not limited to amino, mono- and di-$C_1$-$C_3$ alkylamino, methylphenylamino, methylbenzylamino, $C_1$-$C_3$ alkylamido, carbamamido, ureido, and guanidino).

The term "Heterocyclic aliphatic ring" is intended to mean a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include: halo, cyano, alkyl, heteroalkyl, haloalkyl, phenyl, phenoxy or any combination thereof. More preferred substituents include halo and haloalkyl. Preferred heterocyclic aliphatic rings include piperazinyl, morpholinyl, tetrahydrofuranyl, tetrahydropyranyl and piperidinyl.

The term "Heteroaromatic ring" is intended to mean an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 member atoms in the ring. Bicyclic heteroaromatic rings contain from 8 to 12 member atoms, preferably 9 or 10 member atoms in the ring. Heteroaromatic rings may be unsubstituted or substituted with from 1 to about 4 substituents on the ring. Preferred heteroaromatic ring substituents include: halo, cyano, alkyl, heteroalkyl, haloalkyl, phenyl, phenoxy or any combination thereof. More preferred substituents include halo, haloalkyl, and phenyl. Preferred heteroaromatic rings include thienyl, thiazololyl, purinyl, pyrimidyl, pyridyl, and furanyl. More preferred heteroaromatic rings include thienyl, furanyl, and pyridyl.

The term "Hydroxyalkyl" is intended to mean HO-alkyl.

The term "Phenyl" is intended to mean a six-membered monocyclic aromatic ring which may or may not be substituted with from about 1 to about 4 substituents. The substituents may be substituted at the ortho, meta or para position on the phenyl ring, or any combination thereof. Preferred phenyl substituents include: halo, cyano, alkyl, heteroalkyl, haloalkyl, phenyl, phenoxy or any combination thereof. More preferred substituents on the phenyl ring include halo and haloalkyl. The most preferred substituent is halo. The preferred substitution pattern on the phenyl ring is ortho or meta. The most preferred substitution pattern on the phenyl ring is ortho.

The term "hydrophobic" is intended to mean nonpolar or hydrocarbon-like. Such compounds or groups are essentially composed of carbon and hydrogen atoms and may contain halogen or sulfur.

The term "arginine surrogate" is intended to mean any compound that can be used as a substitute for the arginine amino acid and mimic its effect.

The term "functional derivative" is intended to mean a "chemical derivative", "analog", "fragment", or "variant" biologically active sequence of inhibitors of FP receptor characterized by Formula I or II of the present invention, as well as covalent modifications, including derivatives obtained by reaction with organic derivatizing agents, which derivatives retain at least a portion of the function of the inhibitors characterized by Formula I and II, for example reactivity with an antibody specific for the inhibitor or binding activity mediated through noncatalytic domains, which permits its utility in accordance with the present invention.

The term "chemical derivative" is intended to mean an inhibitor of FP receptor that contains additional chemical moieties not a part of the inhibitors of FP receptor characterized by Formulas I and II. Covalent modifications of Formulas I and II are included within the scope of this invention. Such modifications may be introduced into the molecule by reacting targeted amino acid residues with an organic derivatizing agent that is capable of reacting with selected side chains or terminal residues.

The term "analog" is intended to mean a molecule substantially similar in function to either of the structures characterized by Formula I and II or to biologically active fragment thereof.

The term "fragment" is mended to mean any subset of the structures characterized by Formula I and II, that is, a shorter peptide or peptidomimetic.

The term "variant" is intended to mean to a molecule which is substantially similar to either the entire structure characterized by Formula I, or any fragment thereof, or the entire structure characterized by Formula II, or any fragment thereof. Variant peptides and peptidomimetics may be conveniently prepared by direct chemical synthesis, using methods well known in the art.

BRIEF DESCRIPTION OF THE DRAWINGS

FIG. 1 is a graphic representation of the dose response of THG113 on porcine retinal microvascular contraction. FIG. 1A represents the dose-dependent inhibition of $PGF_{2\alpha}$ produced-contraction by THG113. FIG. 1B represents the determination of the $IC_{50}$ of THG113 in this assay.

FIG. 2 represents the biochemical characterization of THG113.

FIG. 3 represents the effect of THG113 on the contractility of mouse uterine strips immediately after delivery. FIG. 3A is a polygraph recording of contractile responses. The arrows point to the time of addition of THG113 or PGF$_{2\alpha}$. FIGS. 3B AND 3C show a histogram of temporal changes in basal (top) and PGF$_{2\alpha}$ (1 µM)-induced tension.

FIGS. 4A and 4B represent the tocolytic effect of THG113 in a mouse model of infection-related preterm labor.

FIGS. 6A-F show the effect of THG113.31 on contractile properties (duration of contraction and mean tension) of uterine strips obtained from recently-delivered mice in response to 1 µM PGF$_{2\alpha}$ in organ bath assay.

FIG. 7 shows the tocolytic effect of THG113.31 in an endotoxin model of mouse preterm labor.

FIG. 9 shows the tocolytic effect of THG113.706 in an endotoxin model of mouse preterm labor. FIGS. 9A and 9B show the number of animals delivered after 15 h (left panel) and between 24 and 48 h (right panel) after LPS administration. FIG. 9C shows the inhibition (% of maximal contraction produced by 100 nM PGF$_{2\alpha}$) by a dose range of THG113.823-5 in porcine eye cup assays.

DETAILED DESCRIPTION OF THE INVENTION

Figure 2A:
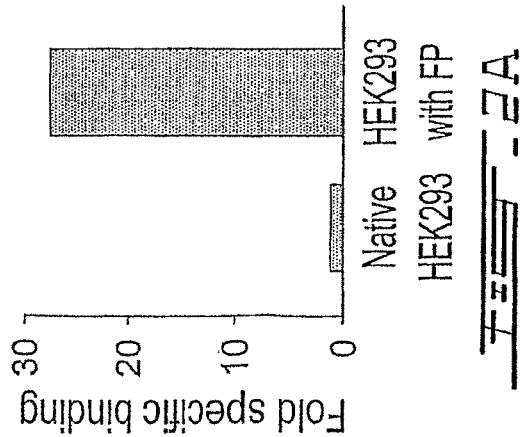
FIG. 2A represents specific binding of [$^{125}$I]-THG113 to cells expressing hFP receptor.
Figure 2B:
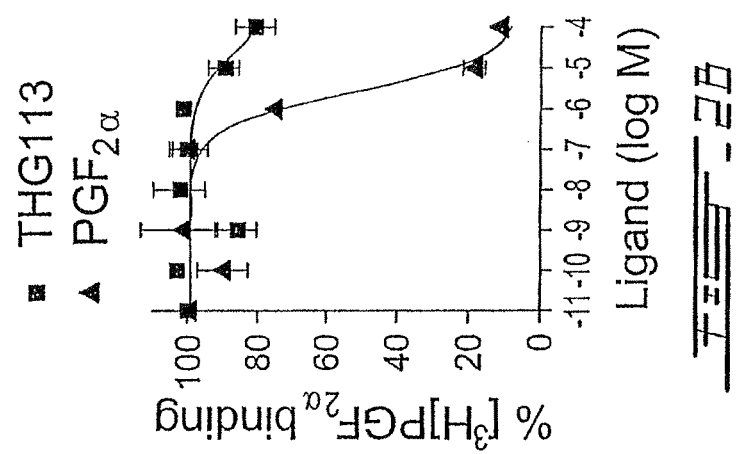
FIG. 2B represents displacement of bound [$^{3}$H] $PGF_{2\alpha}$ by $PGF_{2\alpha}$ or THG113 in FP/293 whole cell assay.
Figure 2C:
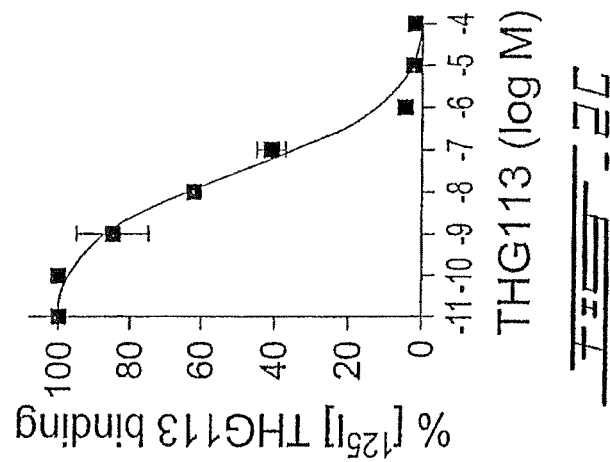
FIG. 2C represents displacement of bound [$^{125}$I]THG113 by THG113 in FP/293 whole cell assay.
Figures 2D, 2E, 2F:
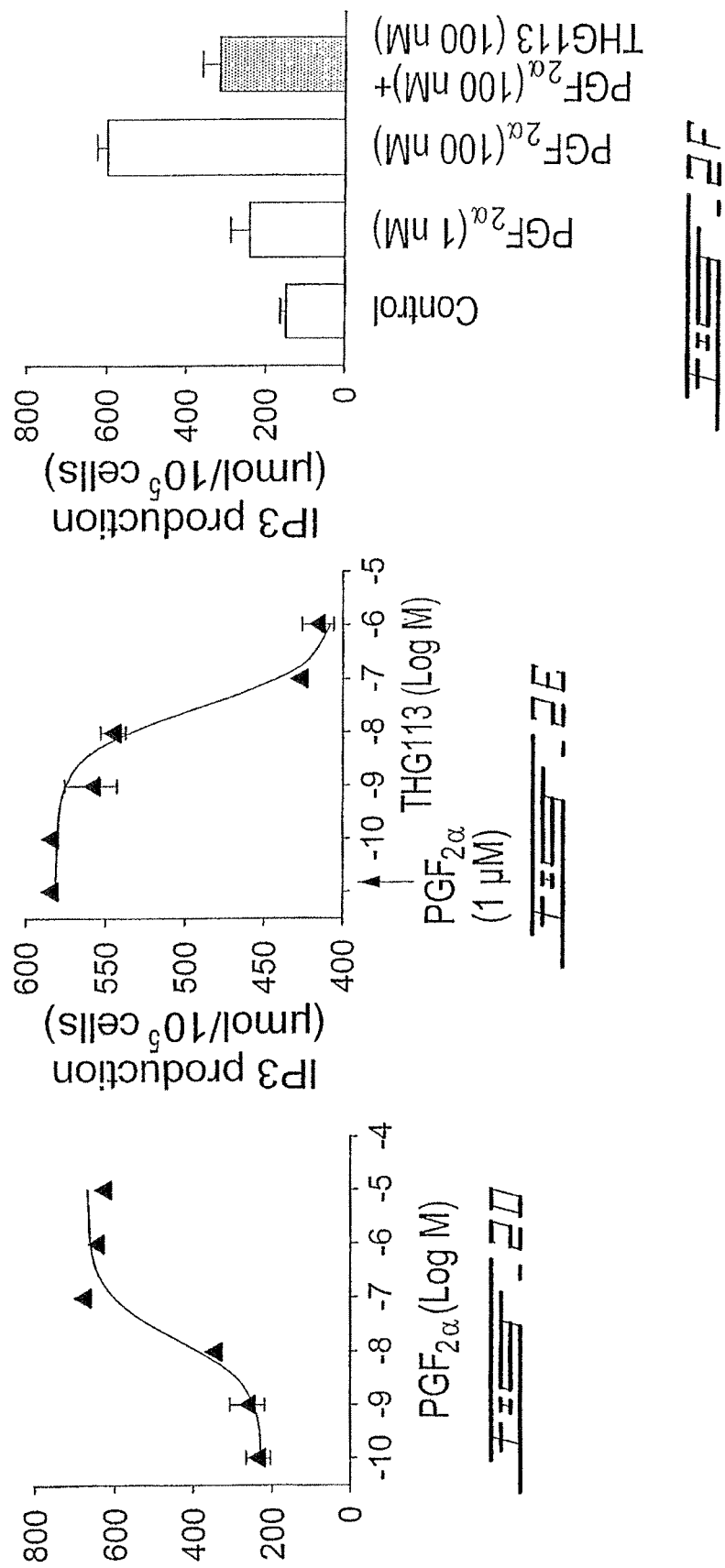
FIG. 2D represents phosphoinositide hydrolysis mediated by $PGF_{2\alpha}$ in FP/293 cells.
FIG. 2E represents phosphoinositide hydrolysis mediated by $PGF_{2\alpha}$ in FP/293 cells in response to incremental doses of THG113 in the presence of 1 µM $PGF_{2\alpha}$.
FIG. 2F is a histogram of effects of THG113 on $PGF_{2\alpha}$-induced phosphoinositide hydrolysis in FP/293 cells.

With a view to provide specific antagonists of FP receptor, screening of short D-peptide libraries was conducted in ex vivo assays of microvascular contraction. Based on this screening, a peptide, THG 113 (SEQ ID NO. 1, Table 4) was selected. In order to identify a more potent analogue of THG113, different amino acid substitutions were made and the biological effects of these substitutions were determined in microvascular contractility assays. From these experiments, several potent analogues of THG113 were identified.

The invention relates to a peptide, wherein the peptide is characterized by Formula I

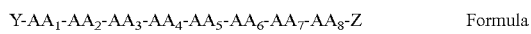

wherein:

Y is attached to the amino-terminus of said peptide and is selected from the group consisting of a hydrogen atom, an acetyl group, a benzoyl group, an acyl group (R—CO—), wherein R is a hydrophobic moiety, or an aroyl group (Ar—CO—), wherein Ar is an aryl group;

Each of AA$_1$ and AA$_2$ are independently selected from the group consisting of no residue, isoleucine (Ile), leucine (Lou), and related alpha-amino acids possessing hydrophobic side-chains;

AA$_3$ is selected from the group consisting of no residue, glycine (Gly), alanine (Ala) and proline (Pro);

AA$_4$ is selected from the group consisting of histidine (His), phenylalanine (Phe), tyrosine (Tyr), tryptophan (Trp) and related alpha-amino acids possessing hydrophobic side-chains;

AA$_5$ is selected from the group consisting of arginine (Arg), ornithine (Orn), lysine (Lys), citruline, 2-, 3-, and 4-pyridylalanine, and arginine surrogates;

AA$_6$ is selected from the group consisting of aspartic acid (Asp), asparagine (Asn), glutamic acid (Glu), glutamine (Gln), serine (Ser), 3-amino-5-phenylpentanoic acid and Phe;

AA$_7$ is selected from the group consisting of no residue, Tyr, Phe, and related alpha-amino acids possessing hydrophobic side-chains, aromatic and arylalkyl amines, and aliphatic amines;

AA$_8$ is selected from the group consisting of no residue, Lys, Leu, Tyr, alpha-amino acids possessing hydrophobic side-chains, and aromatic and aliphatic amines;

Z is attached to the carboxy-terminus of said peptide and is selected from the group consisting of, a hydroxyl group, NH$_2$, and aromatic and aliphatic amines; and functional derivatives thereof.

This invention also includes optical isomers, diastereomers and enantiomers of the formulae above, and pharmaceutically-acceptable salts, biohydrolyzable amides, esters, and imides thereof.

In a preferred embodiment, the acyl group in the definition of Y is selected from the group consisting of benzoyl, acetyl, tert-butyl acetyl, para-phenyl benzoyl, trifluoroacetyl, cyclohexylcarbonyl and phenylacetyl.

In a preferred embodiment, the hydrophobic moiety in the definition of Y is selected from the group consisting of a substituted or unsubstituted alkyl, a substituted or non-substituted cycloalkyl, a phenylmethyl, and a saturated or unsaturated hydrocarbon chain.

In a preferred embodiment, the substituted or unsubstituted alkyl is a saturated hydrocarbon chain having from 1 to 18 C atoms.

In a preferred embodiment, the substituted or unsubstituted alkyl is a saturated hydrocarbon chain having from 1 to 12 C atoms.

In a preferred embodiment, the substituted or unsubstituted alkyl is a saturated hydrocarbon chain having from 1 to 6 C atoms.

In a preferred embodiment, the substituted or unsubstituted alkyl is a saturated hydrocarbon chain having from 1 to 4 C atoms.

In a preferred embodiment, the substituted or unsubstituted alkyl is a linear hydrocarbon chain.

In a preferred embodiment, the substituted or unsubstituted alkyl is a branched hydrocarbon chain.

In a preferred embodiment, the branched hydrocarbon chain has one or two branches.

In a preferred embodiment, the branched hydrocarbon chain has one branch.

In a preferred embodiment, the substituted or unsubstituted alkyl is an unsaturated hydrocarbon chain having 3 to 18 C atoms.

In a preferred embodiment, the unsaturated hydrocarbon chain has at least one double bond and/or at least one triple bond.

In a preferred embodiment, the unsaturated hydrocarbon chain has two double bonds.

In a preferred embodiment, the unsaturated hydrocarbon chain has one double bond.

In a preferred embodiment, the unsaturated hydrocarbon chain has one triple bond.

In a preferred embodiment, the substituted alkyl is selected from the group consisting of a mono-, a di- and a tri-substituted alkyl.

In a preferred embodiment, the substituted alkyl is substituted with from 1 to 4 substituents.

In a preferred embodiment, the substituent is selected from the group consisting of halo, haloalkyl, hydroxy, aryl, heterocyclyl and heteroaryl.

In a preferred embodiment, the aryl is selected from the group consisting of phenyl, tolyl, alkyloxyphenyl, alkyloxycarbonylphenyl, and halophenyl.

In a preferred embodiment, the substituted or unsubstituted cycloalkyl is a saturated ring of from 3 to 8 C atoms.

In a preferred embodiment, the substituted or unsubstituted cycloalkyl is selected from the group consisting of cyclopentyl and cyclohexyl.

In a preferred embodiment, the substituted cycloalkyl is selected from the group consisting of mono- and di-substituted cycloalkyl.

In a preferred embodiment, the substituted cycloalkyl has substituents selected from the group consisting of halo, haloalkyl, hydroxy, aryl, heterocyclyl and heteroaryl.

In a preferred embodiment, the aryl is selected from the group consisting of phenyl, tolyl, alkoxyphenyl, alkoxycarbonylphenyl and halophenyl.

In a preferred embodiment, the saturated or unsaturated hydrocarbon chain is selected from the group consisting of a linear saturated or unsaturated alkyl group, an alkenyl group, and branched saturated or unsaturated alkyl group.

In a preferred embodiment, the linear saturated alkyl group has from 1 to 18 C atoms.

In a preferred embodiment, the linear saturated alkyl group has from 1 to 12 C atoms.

In a preferred embodiment, the linear saturated alkyl group has from 1 to 6 C atoms.

In a preferred embodiment, the linear saturated alkyl group has from 1 to 4 C atoms.

In a preferred embodiment, the alkenyl group has 3 to 8 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, in the definition of $AA_4$, the hydrophobic side-chain is selected from the group consisting of cyclohexylalanine and heterocyclic side-chains.

In a preferred embodiment, the heterocyclic side-chain is a pyridylalanine group.

In a preferred embodiment, in the definition of $AA_7$, $AA_8$ and Z, the aromatic amine is selected from the group consisting of phenylmethylamine, phenylethylamine, phenylproplyamine, and an amine comprising a saturated or unsaturated hydrocarbon chain.

In a preferred embodiment, in the definition of $AA_7$, $AA_8$ and Z, the aliphatic amine is selected from the group consisting of amines comprising a saturated or unsaturated hydrocarbon chain.

In a preferred embodiment, the amine comprising a saturated or unsaturated hydrocarbon chain is a primary amine.

In a preferred embodiment, the saturated or unsaturated hydrocarbon chain is selected from the group consisting of a linear saturated or unsaturated alkyl group, an alkenyl group, and a branched saturated or unsaturated alkyl group.

In a preferred embodiment, the linear saturated alkyl group has from 1 to 18 carbon atoms and said linear unsaturated alkyl group has 3 to 18 C atoms.

In a preferred embodiment, the linear saturated alkyl group has from 1 to 12 carbon atoms and said linear unsaturated alkyl group has 3 to 12 C atoms.

In a preferred embodiment, the linear saturated alkyl group has from 1 to 6 carbon atoms and said linear unsaturated alkyl group has 3 to 6 C atoms.

In a preferred embodiment, the linear saturated alkyl group has from 1 to 4 carbon atoms and said linear unsaturated alkyl group has 3 to 4 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, in the definitions of $AA_1$ to $AA_8$, the amino acids are D- or L-amino acids.

In a preferred embodiment, in the definition of $AA_7$, $AA_8$ and Z, the aromatic amine is a primary aromatic amine.

In a preferred embodiment, in the definition of $AA_7$, the primary arylalkyl amine has a ring of from 6 to 10 C atoms.

In a preferred embodiment, in the primary arylalkyl amine, the aryl is selected from the group consisting of phenyl, tolyl, alkoxyphenyl, alkoxycarbonylphenyl and halophenyl.

In a preferred embodiment, the primary aromatic amine has a ring of from 6 to 10 C atoms.

In a preferred embodiment, in the definition of $AA_7$, $AA_8$ and Z the aliphatic amine is a primary aliphatic amine.

In a preferred embodiment, the primary aliphatic amine has from 1 to 18 C atoms.

In a preferred embodiment, the peptide is selected from the group consisting of SEQ ID NO 1-4, 6, 8-11, 13-32, and functional derivatives thereof.

In a preferred embodiment, the peptide and functional derivatives thereof substantially inhibit FP receptor.

In a preferred embodiment, the FP receptor is from a mammal.

In a preferred embodiment, the mammal is a human.

In a preferred embodiment, the inhibition of FP receptor is measured according to porcine retinal microvascular contraction to prostaglandin $F_2$, wherein the inhibition is at least 50% of that produced by the ligand in the absence of the inhibitor.

In a preferred embodiment, the peptide has an inhibition of the FP receptor measured according to porcine retinal microvascular contraction to prostaglandin $F_{2\alpha}$, wherein the inhibition is at least 50% of that produced by the ligand in the absence of the inhibitor.

The invention also relates to a pharmaceutical composition comprising a therapeutically effective amount of at least one peptide of SEQ ID NO 1-4, 6, 8-11, 13-32, and functional derivatives thereof, in association with a pharmaceutically acceptable carrier.

In a preferred embodiment, the therapeutically effective amount of the peptide is 0.1-100 mg/Kg body weight.

In a preferred embodiment, the peptide is used alone or in combination with a pharmaceutically acceptable carrier, to inhibit FP receptor.

In a preferred embodiment, the pharmaceutical composition is used for the preparation of a medicament to arrest preterm labor.

In a preferred embodiment, the pharmaceutical composition is used for the preparation of a medicament for the treatment of dysmenorrhea.

The invention also relates to a method of arresting preterm labor comprising administering to an individual a therapeutically effective amount of pharmaceutical composition comprising at least one peptide of SEQ ID NO 1-4, 6, 8-11, 13-32, and functional derivatives thereof, in association with a pharmaceutically acceptable carrier.

The invention also relates to a method of treating dysmenorrhea comprising administering to an individual a therapeutically effective amount at least one peptide of SEQ ID NO 1-4, 6, 8-11, 13-32, and functional derivatives thereof, in association with a pharmaceutically acceptable carrier.

Conservative substitutions of the amino acids of THG113 of the present invention includes a variant wherein at least one amino acid residue in the polypeptide has been conservatively replaced by a different amino acid. Such substitutions preferably are made in accordance with the following list as presented in Table 1. The biological effects of such substitutions may be determined by FP receptor binding and activity assays.

TABLE 1

Examples of substitutions of amino acids in peptides and proteins

| Original Residue | Example of Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of THG113 of the present invention are those in which at least one amino acid residue has been removed and a different residue inserted in its place according to Table 2. Alternative conservative substitutions are defined herein as exchanges within one of the five groups presented in Table 2.

TABLE 2

Alternative conservative substitutions

| Small aliphatic, nonpolar or slightly polar residues | Ala, Ser, Thr (Pro, Gly) |
|---|---|
| Polar, negatively charged residues and their amides | Asp, Asn, Glu, Gln |
| Polar, positively charged residues | His, Arg, Lys |

TABLE 2-continued

Alternative conservative substitutions

| Large aliphatic, nonpolar residues | Met, Leu, Ile, Val (Cys) |
|---|---|
| Large aromatic residues | Phe, Tyr, Trp |

The three amino acid residues in parentheses above have special roles in protein architecture. Gly is the only residue lacking any side chain and thus imparts flexibility to the chain. This however tends to promote the formation of secondary structure other than alpha-helical. Proline, because of its unusual geometry, tightly constrains the chain. It generally tends to promote beta turn-like structures. Cystine is capable of participating in disulfide bond formation. Note also that Tyr, because of its hydrogen bonding potential, has significant kinship with Ser Thr, and similar amino acids.

The biological effects of these amino acid changes in the peptide cannot be predicted with certainty in the absence of a detailed tertiary structure of the binding site on the receptor. To date no GPCR other than bovine rhodopsin has yielded that detailed tertiary structure. Hence those skilled in the art will appreciate that the modified peptides should be tested by bioassays to confirm biological activity, such as receptor binding or modulation of ligand binding to the corresponding GPCR. Specific examples pertaining to FP receptor in terms of in vitro, ex vivo and in vivo assays are given below.

The invention also relates to a peptidomimetic characterized by Formula II:

$$Y\text{-BTM-AA}_1\text{-AA}_2\text{-AA}_3\text{-Z} \qquad \text{Formula II}$$

wherein:

Y is attached to the amino-terminus of the peptide and is selected from the group consisting of a hydrogen atom, an acyl group (R—CO—), wherein R is a hydrophobic moiety, or an aroyl group (Ar—CO—), wherein Ar is an aryl group;

BTM (beta turn mimetic) is a dipeptide surrogate;

$AA_1$ is selected from the group consisting of Arg, Orn, Lys, citruline, 2-, 3-, and 4-pyridylalanine, and arginine surrogates;

$AA_2$ is selected from the group consisting of Asp, Asn, Glu, Gln, Ser, 3-amino-5-phenylpentanoic acid and Phe;

$AA_3$ is selected from the group consisting of no residue, Tyr, Phe, and related alpha-amino acids possessing hydrophobic side-chains, and aromatic amines, aliphatic amines and primary arylalkyl amines;

Z is selected from the group consisting of no residue, a hydroxyl group, $NH_2$, and aromatic, heteroaromatic and aliphatic amines; and functional derivatives thereof.

In a preferred embodiment, the acyl group in the definition of Y is selected from the group consisting of benzoyl, acetyl, tert-butyl acetyl, para-phenyl benzoyl, trifluoroacetyl, cyclohexylcarbonyl and phenylacetyl.

In a preferred embodiment, the hydrophobic moiety in the definition of Y is selected from the group consisting of a substituted or non-substituted alkyl, a substituted or non-substituted cycloalkyl, a phenylmethyl, and a saturated or unsaturated hydrocarbon chain.

In a preferred embodiment, the substituted or unsubstituted alkyl is a saturated hydrocarbon chain having from 1 to 18 C atoms.

In a preferred embodiment, the substituted or unsubstituted alkyl is a saturated hydrocarbon chain having from 1 to 12 C atoms.

In a preferred embodiment, the substituted or unsubstituted alkyl is a saturated hydrocarbon chain having from 1 to 6 C atoms.

In a preferred embodiment, the substituted or unsubstituted alkyl is a saturated hydrocarbon chain having from 1 to 4 C atoms.

In a preferred embodiment, the substituted or unsubstituted alkyl is a linear hydrocarbon chain.

In a preferred embodiment, the substituted or unsubstituted alkyl is a branched hydrocarbon chain.

In a preferred embodiment, the branched hydrocarbon chain has one or two branches.

In a preferred embodiment, the branched hydrocarbon chain has one branch.

In a preferred embodiment, the substituted or unsubstituted alkyl is an unsaturated hydrocarbon chain having from 3 to 18 C atoms.

In a preferred embodiment, the unsaturated hydrocarbon chain has at least one double bond and/or at least one triple bond.

In a preferred embodiment, the unsaturated hydrocarbon chain has two double bonds.

In a preferred embodiment, the unsaturated hydrocarbon chain has one double bond.

In a preferred embodiment, the unsaturated hydrocarbon chain has one triple bond.

In a preferred embodiment, the substituted alkyl is selected from the group consisting of a mono-, a di-, and a tri-substituted alkyl.

In a preferred embodiment, the substituted alkyl is substituted with from 1 to 4 substituents.

In a preferred embodiment, the substituent is selected from the group consisting of halo, haloalkyl, hydroxy, aryl, heterocyclyl and heteroaryl.

In a preferred embodiment, the aryl is selected from the group consisting of phenyl, tolyl, alkyloxyphenyl, alkyloxycarbonylphenyl, and halophenyl.

In a preferred embodiment, the substituted or unsubstituted cycloalkyl is a saturated ring of from 3 to 8 C atoms.

In a preferred embodiment, the substituted or unsubstituted cycloalkyl is selected from the group consisting of cyclopentyl and cyclohexyl.

In a preferred embodiment, the substituted cycloalkyl is selected from the group consisting of mono- and di-substituted cycloalkyl.

In a preferred embodiment, the substituted cycloalkyl has substituents selected from the group consisting of halo, haloalkyl, hydroxy, aryl, heterocyclyl and heteroaryl.

In a preferred embodiment, the aryl is selected from the group consisting of phenyl, tolyl, alkoxyphenyl, alkoxycarbonylphenyl and halophenyl.

In a preferred embodiment, the saturated or unsaturated hydrocarbon chain is selected from the group consisting of a linear saturated or unsaturated alkyl group, an alkenyl group, and a branched saturated or unsaturated alkyl group.

In a preferred embodiment, the linear saturated alkyl group has from 1 to 18 carbon atoms.

In a preferred embodiment, the linear saturated alkyl group has from 1 to 12 carbon atoms.

In a preferred embodiment, the linear saturated alkyl group has from 1 to 6 carbon atoms.

In a preferred embodiment, the linear saturated alkyl group has from 1 to 4 carbon atoms.

In a preferred embodiment, the alkenyl group has 3 to 8 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, in the definition of $AA_3$ and Z, the aliphatic amine is selected from the group consisting of amines comprising a saturated or unsaturated hydrocarbon chain.

In a preferred embodiment, the amine comprising a saturated or unsaturated hydrocarbon chain is a primary amine.

In a preferred embodiment, the saturated or unsaturated hydrocarbon chain is selected from the group consisting of a linear saturated or unsaturated alkyl group, an alkenyl group, and a branched saturated or unsaturated alkyl group.

In a preferred embodiment, the linear saturated alkyl group has from 1 to 18 carbon atoms and the linear unsaturated alkyl group has 3 to 18 C atoms.

In a preferred embodiment, the linear saturated alkyl group has from 1 to 12 carbon atoms and the linear unsaturated alkyl group has 3 to 12 C atoms.

In a preferred embodiment, the linear saturated alkyl group has from 1 to 6 carbon atoms and the linear unsaturated alkyl group has 3 to 6 C atoms.

In a preferred embodiment, the linear saturated alkyl group has from 1 to 4 carbon atoms and the linear unsaturated alkyl group has 3 to 4 C atoms.

In a preferred embodiment, the branched saturated or unsaturated alkyl group has from 3 to 18 C atoms.

In a preferred embodiment, the branched saturated or unsaturated alkyl has one or two branches.

In a preferred embodiment, the branched saturated or unsaturated alkyl has one branch.

In a preferred embodiment, the linear unsaturated alkyl or branched unsaturated alkyl has at least one double bond and/or at least one triple bond.

In a preferred embodiment, the linear unsaturated alkyl or branched unsaturated alkyl has two double bonds.

In a preferred embodiment, the linear unsaturated alkyl or branched unsaturated alkyl has one double bond.

In a preferred embodiment, the linear unsaturated alkyl or branched unsaturated alkyl has one triple bond.

In a preferred embodiment, the dipeptide surrogate is selected from the group consisting of indolizidinone amino acids (Lombart and Lubell 1996 *J. Org. Chem.* 61: 9437-9446; Gosselin and Lubell 1998 *J. Org. Chem.* 63: 7463-7471), 5- and 7-alkyl-branched indolizidinone amino acids (Polyak and Lubell 1998 *J. Org. Chem.* 63: 5937-5949), quinolizidinone amino acids and pyrroloazepinone amino acids (Gosselin and Lubell 2000 *J. Org. Chem.* 2163-2171), azabicyclo[X.Y.0]alkanone amino acids (reviewed in Hannessian at al. 1997 *Tetrahedron* 53: 12789-12854), heterocyclic and carbocyclic moieties, mimics of beta-turn structure and lactam analogs (Aubé, J. In Advances in Amino Acid Mimetics and Peptidomimetics, Abell, A., Ed., JAI Press, Greenwitch, 1997, Vol. 2, pp 193-232; MacDonald and Aubé 2001 *Curr. Org. Chem.* 5: 417-438).

In a preferred embodiment, in the definitions of $AA_1$ to $AA_3$, the amino acids are D- or L-amino acids.

In a preferred embodiment, in the definition of $AA_3$ and Z, the aromatic amine is a primary aromatic amine.

In a preferred embodiment, in the definition of $AA_3$, the primary arylalkyl has a ring of from 6 to 10 C atoms.

In a preferred embodiment, in the primary arylalkyl, the aryl is selected from the group consisting of phenyl, tolyl, alkoxyphenyl, alkoxycarbonylphenyl and halophenyl.

In a preferred embodiment, the primary aromatic amine has a ring of from 6 to 10 C atoms.

In a preferred embodiment, in the definition of $AA_3$ and Z the aliphatic amine is a primary aliphatic amine.

In a preferred embodiment, the primary aliphatic amine has from 1 to 10 C atoms.

In a preferred embodiment, the peptidomimetic is selected from the group consisting of compounds numbered 33-52 as shown in Table 5, and functional derivatives thereof.

In a preferred embodiment, the peptidomimetic and functional derivatives thereof substantially inhibit FP receptor.

In a preferred embodiment, the FP receptor is from a mammal.

In a preferred embodiment, the mammal is a human.

In a preferred embodiment, the inhibition of FP receptor is measured according to porcine retinal microvascular contraction to prostaglandin $F_{2\alpha}$, wherein the inhibition is at least 50% of that produced by the ligand in the absence of the peptidomimetic.

In a preferred embodiment, the peptidomimetic has an inhibition of the FP receptor measured according to porcine retinal microvascular contraction to prostaglandin $F_{2\alpha}$, wherein the inhibition is at least 50% of that produced by the ligand in the absence of the peptidomimetic.

The invention also relates to a pharmaceutical composition comprising a therapeutically effective amount of at least one compound numbered 33-52 as shown in Table 5, and functional derivatives thereof, in association with a pharmaceutically acceptable carrier.

In a preferred embodiment, the therapeutically effective amount of the peptidomimetic is 0.1-100 mg/Kg body weight.

In a preferred embodiment, the peptidomimetic is used alone or in combination with a pharmaceutically acceptable carrier, to inhibit FP receptor.

In a preferred embodiment, the pharmaceutical composition is used for the preparation of a medicament to arrest preterm labor.

In a preferred embodiment, the pharmaceutical composition is used for the preparation of a medicament for the treatment of dysmenorrhea.

The invention also relates to a method of arresting preterm labor comprising administering to an individual a therapeutically effective amount of pharmaceutical composition comprising at least one compound numbered 33-52 as shown in Table 5, and functional derivatives thereof, in association with a pharmaceutically acceptable carrier.

The invention also relates to a method of treating dysmenorrhea comprising administering to an individual a therapeutically effective amount of at least one compound numbered 33-52 as shown in Table 5, and functional derivatives thereof, in association with a pharmaceutically acceptable carrier.

Covalent modifications of the peptide are thus included within the scope of the present invention. Such modifications may be introduced into THG113 and its derivatives by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphthylalanine, D- or L-phenylglycine, D- or L-2-thienylalanine, D- or L-1-, 2-, 3- or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines where alkyl may be substituted or unsubstituted methyl, ethyl, propyl, hexyl, butyl, pentyl, isopropyl, isobutyl, or iso-pentyl groups.

Non-carboxylate amino acids can be made to possess negative charge, such as the non-limiting examples of phosphono- or sulfated (e.g. $—SO_3H$) amino acids.

Other substitutions may include unnatural alkylated amino acids which are made by combining "alkyl" with any natural amino acid. Basic natural amino acids such as lysine, arginine may be substituted with alkyl groups at $NH_2$. Others are nitrile derivatives (e.g., containing the CN-moiety in place of $CONH_2$) of asparagine or glutamine, and sulfoxide derivative of methionine. Methods of preparation of such amino acid derivatives are well known to one skilled in the art.

In addition, any amide linkage in THG113 and its derivatives can be replaced by a ketomethylene, hydroxyethyl, ethyl/reduced amide, thioamide or reversed amide moieties, e.g. (—C=O)—$CH_2$—), (—CHOH)—$CH_2$—), ($CH_2$—$CH_2$—), (—C=S)—NH—), or (—NH—(—C=O) for (—C=O)—NH—).

In addition, any amino acid representing a component of said peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Additional amino acid modifications of amino acids in THG113 and its derivatives of the present invention may include the following: cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidazolyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain; para-bromophenacyl bromide may also be used, e.g., where the reaction is preferably performed in 0.1 M sodium cacodylate at pH 6.0.

Lysinyl and amino terminal residues may be reacted with compounds such as succinic or other carboxylic acid anhydrides. Other suitable reagents for derivatizing alpha-amino-containing residues include compounds such as imidoesters, e.g. methyl picolinimidate; pyridoxal phosphate; pyridoxal; chloroborohydride; trinitrobenzenesulfonic acid; O-methylisourea; 2,4 pentanedione; and transaminase-catalyzed reactions with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Other modifications of THC113 and its derivatives of the present invention may include hydroxylation of proline and lysine, phosphorylation of hydroxyl groups of seryl or threonyl residues, methylation of the alpha-amino groups of lysine, arginine, and histidine, side chain acetylation of the N-terminal amine, methylation of main chain amide residues (or substitution with N-methyl amino acids) and, in some instances, amidation of the C-terminal carboxyl groups, according to known method steps.

The invention also relates to a method of arresting uterine contractions associated with labor with a view to prolong gestation. Furthermore, the method comprises administering to an individual a pharmaceutical composition comprising a FP receptor antagonist of the present invention.

The invention also relates to a method of arresting uterine spasms associated with dysmenorrhea in which the individual diagnosed with dysmenorrhea is administered a pharmaceutical composition comprising a FP receptor antagonist of the present invention.

The present invention will be more readily understood by referring to the following examples which are given to illustrate the invention rather than to limit its scope.

The following examples illustrate the pharmacological efficacy and potency of THG113 antagonism on FP receptor and its biochemical and physiological responses.

Dose Response of THG113 on Porcine Retinal Microvascular Contraction

In order to see if THG113 could inhibit FP receptor function in an ex vivo system, we chose the porcine eyecup model, an ex vivo assay of vascular constriction in porcine retinas which we previously described and validated (Li et al. 1996 *J Pharmacol Exp Ther.* 278(1):370-7). Since FP receptor densities in newborn vasculature are minimal due to down regulation by high levels of circulating prostaglandins in the perinatal period, the newborn pigs were treated with a prostaglandin synthase blocker, ibuprofen (30 mg/Kg of bodyweight/8 h for 24 h) to increase the density of the receptors as well as their vasomotor effects. By inhibiting circulating prostaglandins, we were able to show potent inhibition of FP receptor-mediated second messenger synthesis as well as FP-mediated vascular constriction in this eyecup model.

To prepare eyecups, a circular incision was made 3-4 mm posterior to ora serrata to remove the interior segment and vitreous body with minimal handling of the retina. The remaining eyecup was fixed with pins to a wax base in a 20 ml tissue bath containing 20 ml of Kreb's buffer (pH 7.35-7.45) and equilibrated with 21% oxygen and 5% carbon dioxide at 37° C. The preparations were allowed to stabilize for 30 min. Peptides at 100 μM were added and incubation was continued for 20 min before the addition of $PGF_{2\alpha}$.

Cumulative concentration-response curves of $PGF_{2\alpha}$ or the antagonists ($10^{-10}$ to $10^{-5}$ M) were constructed. To assess the reversibility of the antagonists, the eyecups were thoroughly washed (which would wash away the peptide) with incubation medium and concentration response curves for $PGF_{2\alpha}$ were determined. The outer vessel diameter was recorded with a video camera mounted on a dissecting microscope (Zeiss M 400) and the responses were quantified by a digital image analyzer (Sigma Scan Software, Jandel Scientific, Corte Madera, Calif.). Vascular diameter was recorded before and 5 min following the topical application of the agonist. Each measurement was repeated three times and showed <1% variability.

As shown in FIG. 1 there was dose-dependent inhibition of $PGF_{2\alpha}$ produced-contraction (0.1 μM, physiological concentration) by THG113, and at 100 μM THG113 even supraphysiological levels of $PGF_{2\alpha}$ failed to produce contractile response (FIG. 1A). The calculated $IC_{50}$ of THG113 in this assay is 340 nM (FIG. 1B).

The selectivity of THG113 to FP receptor was assessed by measuring microvascular contractile responses to several G protein coupled receptors (GPCRs) (in parenthesis) for $PGF_{2\alpha}$ (FP), $PGE_2$ (EPA, $TxA_2$ (TP), Phenylephrine (Alpha-1-adrenergic), Endothelin ($ET_A$), angiotensin-II ($AT_1$), and acetylcholine (uncharacterized subtypes) in the presence of 0.1 mM THG113; BHQ was used to show that the intracellular $Ca^{2+}$ dynamics were unaltered by THG113 (Table 3). At 0.1 μM concentration of the agonists, the inhibition of THG113 was selective for FP receptor only.

TABLE 3

Selectivity of THG113 inhibition to FP receptor

| | % Inhibition | |
|---|---|---|
| Agonist | $10^{-6}$M | $10^{-7}$M |
| $PGF_{2\alpha}$ (FP) | 90.4 | 85 |
| 17-phenyl trinor PGE2 ($EP_1$) | 16.7 | <1 |
| U46619 (TP) | <1 | |
| C-PAF | <1 | <1 |
| Phenylephrine ($a_1$-AR) | <1 | |
| Urotensin | <1 | |
| Endothelin ($ET_A$) | <1 | |
| Angiotensin-II | <1 | |
| Acetylcholine | <1 | |
| BHQ (SR $Ca^{2+}$ ATPase inhibitor) | <1 | |

Biochemical Characterization of THG113

The biochemical characterization of THG113 is shown in FIG. 2. [$^{125}$I]-THG113 was produced by labeling tyrosine residue with [$^{125}$I] using the lactoperoxidase method (Thorell et al. 1971 Biochim. Biophys. Acta 28, 251(3):363-369). HEK293 cells ectopically expressing cloned human FP receptor, FP/293, ($10^5$) were incubated with [$^{125}$I]-THG113 ($10^6$ cpm) for 1 h; bound and unbound ligands were separated by filtration on glass fibre filters. The radioactivity on the filters was counted by scintillation spectrophotometry. For a detailed method of ligand binding and displacement, see Li at al. (1996). Very little specific binding of [$^{125}$I]-THG113 to parent HEK293 cells and 27 fold more specific binding to FP/293 cells was observed (FIG. 2A), suggesting that THG113 specifically bound to human FP protein. Using cloned FP/293 cells in binding assays (see Li et al. for a method of ligand displacement assay), the specific binding of THG113 to FP protein was investigated. [³H]PGF$_{2\alpha}$ binding was completely displaced by cold PGF$_{2\alpha}$ (FIG. 2B), but little displacement of [³H]PGF$_{2\alpha}$ by THG113 was detected (FIG. 2C).

FP/293 cells were labelled with [³H] myoinositol for 24 h and stimulated with PGF$_{2\alpha}$ (FIG. 2D) or THG113 (FIG. 2E) in the presence of 100 nM PGF$_{2\alpha}$ for 30 min. The phosphoinositides were collected by anion exchange chromatography with 1 M ammonium formate/0.1 N formic acid. A sigmoidal dose response of IP hydrolysis to PGF$_{2\alpha}$ was obtained with an EC$_{50}$ of 20 nM (D). THG113 dose-dependently inhibited PGF$_{2\alpha}$-stimulated phosphoinositide hydrolysis (E and F).

Effect of THG113 on the Contractility of Mouse Uterine Strips Immediately after Delivery Myometrial strips (1 cm) were dissected from pregnant mice immediately after delivery (when the uterus is still non-quiescent) and suspended in organ baths containing 10 ml of KREB's buffer bubbled with 90% oxygen. Contractile responses were recorded using pressure transducers connected to a Gould polygraph. Arrows point to the time of addition of THG113 or PGF$_{2\alpha}$. As shown in the left panel, both spontaneous as well as PGF$_{2\alpha}$ (1 µM)-induced contractile responses were diminished within 20 min after the addition of 100 µM THG113. The right panel shows temporal changes in basal (top) and PGF$_{2\alpha}$ (1 µM)-induced tension.

Tocolytic Effect of THG113 in a Mouse Model of Infection-Related Preteen Labor

Figure 5A:
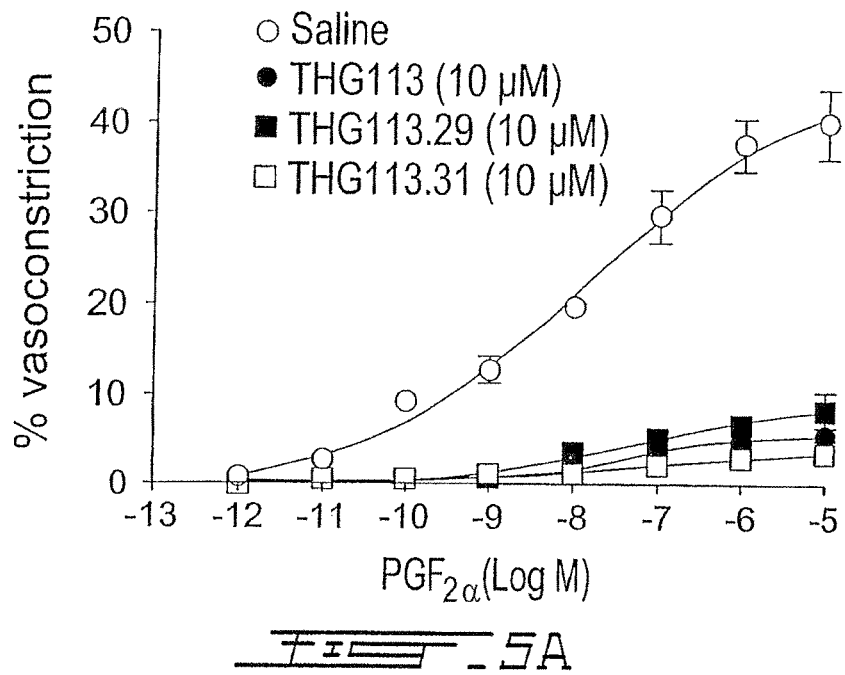
FIG. 5 shows the dose-response curves of microvascular contractility FIG. 5A to PGF$_{\alpha}$ in the presence/absence of THG113 and its derivatives (10 µM) in porcine eye cup assay. All compounds inhibited PGF$_{2\alpha}$-induced responses even at high concentrations of the agonist.
FIG. 5D Inhibitory response of increasing doses of THG113 and its derivatives on porcine ocular contractility induced by 1 µM PGF$_{2\alpha}$.
Figure 5B:
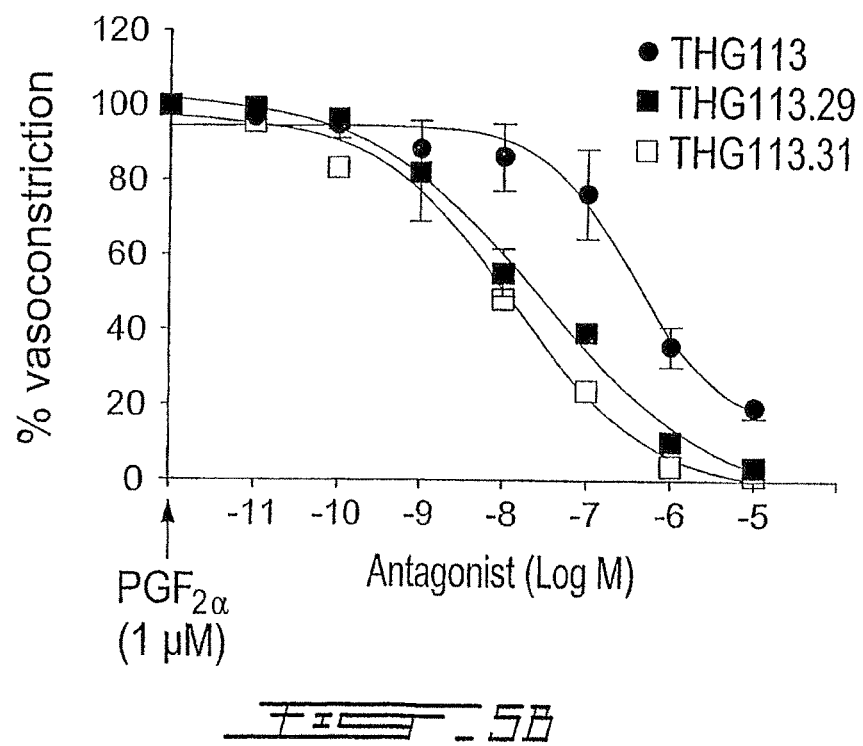
Figure 7A:
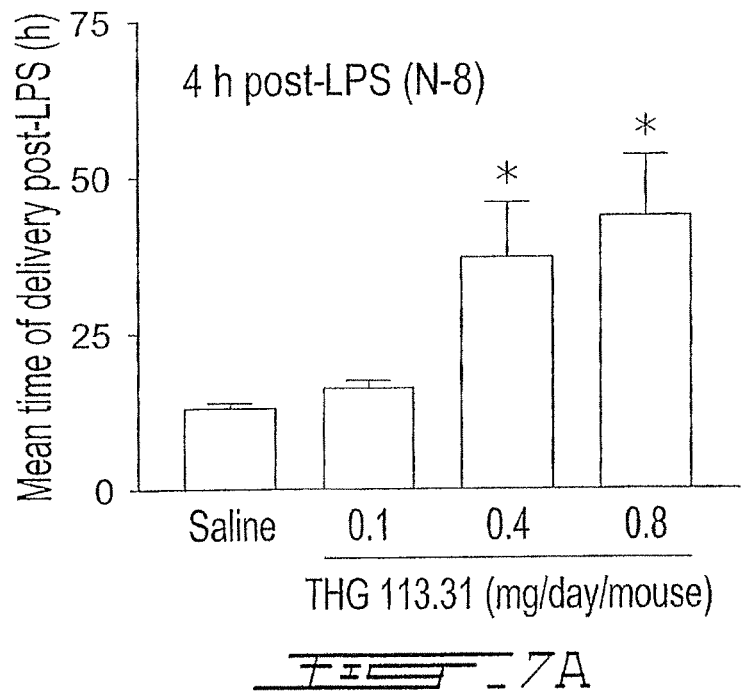
FIG. 7A shows the mean time (h) of delivery after LPS administration.
Figure 7B:
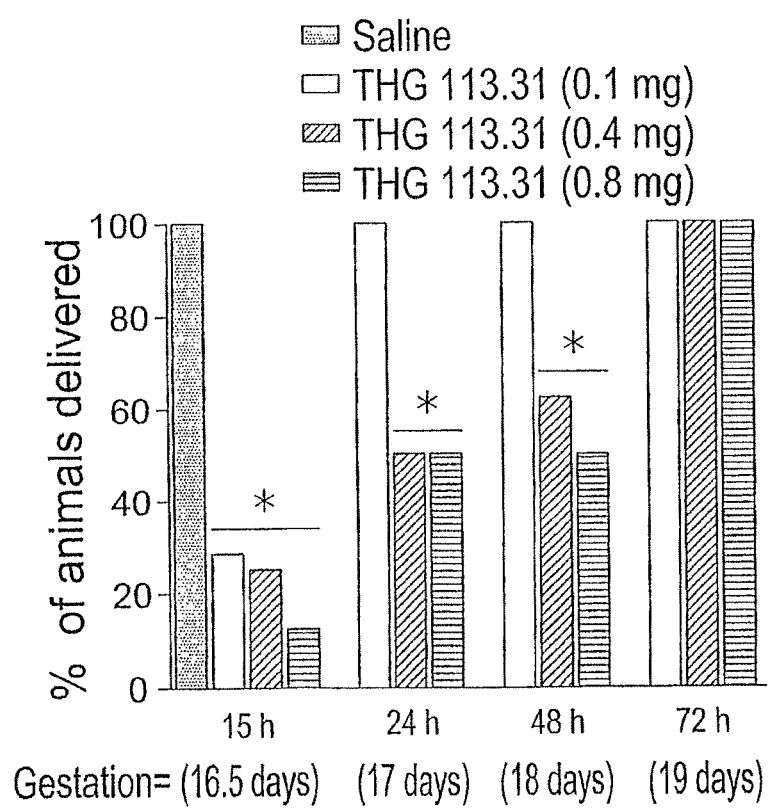
FIG. 7B shows the percentage of animals delivered at 15, 24, 48 and 72 h after LPS administration.

Timed-pregnant CD-1 mice (mean gestation was 19.2 days) were purchased and at day 17, alzet pumps containing THG113 in saline were surgically implanted on the back of the animals. These pumps continuously deliver the inhibitor at 1 mg/day. *E. coli* lipopolysaccharide (LPS) (50 µg i. p. twice at 3 h interval) was injected on day 15. Saline-treated animals delivered within 15 h of LPS administration, whereas THG113 treatment delayed labor in 60% of animals past 15 h; the mean time of delivery in THG113-treated animals was 36 h (FIG. 5).

Effects of THG113 Derivatives in Porcine Microvascular Contraction Assay

The effects of THG113 derivatives on porcine retinal microvascular contraction are shown in Table 4. The percent (%) inhibition denotes porcine ocular microvessel contraction in response to 100 nM PGF$_{2\alpha}$ in the presence of 0.1 mM peptide, relative to that in the absence of the peptide, expressed as percentage.

TABLE 4

Effects of FP receptor inhibitors in porcine microvascular contraction assay

| Compound No | Peptide name | Sequence (N to C) | % inhibition |
|---|---|---|---|
| 1 | THG113 | i l g h r d y k | 80 |
| 2 | THG113.1 | g h r d y k | 37 |
| 3 | THG113.2 | i l g a r d y k | 10 |
| 4 | THG113.3 | i l g h a d y k | 38 |
| 5 | THG113.4 | i l g h r a y k | 0 |
| 6 | THG113.5 | i l g H r a y k | 65 |
| 7 | THG113.6 | i l g h R d e k | 0 |
| 8 | THG113.7 | i l g h r D y k | 36 |
| 9 | THG113.8 | i l a h r d y k | 76 |
| 10 | THG113.9 | i l A h r d y k | 53 |
| 11 | THG113.10 | i l g h r d y w | 23 |
| 12 | THG113.11 | i l g h r d e k | 0 |
| 13 | THG113.12 | i l g f r d y k | 87 |
| 14 | THG113.13 | i l g h r e y k | 43 |
| 15 | THG113.14 | i l g h k d y k | 63 |
| 16 | THG113.15 | i l g h r n y k | 60 |
| 17 | THG113.16 | i l g h r d y | 13 |
| 18 | THG113.17 | i l p h r d y k | 45 |
| 19 | THG113.18 | i l h r d y k | 13 |
| 20 | THG113.19 | i l g h q d y k | 70 |
| 21 | THG113.20 | i l g h r s y k | 25 |
| 22 | THG113.21 | i l g h r d y-amide | 50 |
| 23 | THG113.22 | l i g h r d y k-amide | 54 |
| 24 | THG113.23 | i l g w r d y k | 83 |
| 25 | THG113.24 | i l g y r d y k | 49 |
| 26 | THG113.25 | i l g-(cha)-r d y k | 94 |
| 27 | THG113.26 | i l g (cha) g d y k | 21 |
| 28 | THG113.27 | i l g (cha) r n y k | 54 |
| 29 | THG113.28 | k y d r h g l l | 47 |
| 30 | THG113.29 | i l g h-(3PA)-q d y k | >85 |
| 31 | THG113.30 | i l g h-(4PA)-d y k | >85 |
| 32 | THG113.31 | i l g h (cit) d y k | >85 |

Small letters: D-amino acids;
capital letters: L-amino acids; cha: D-cyclohexylalanine; PA: L-pyridylalanine; cit: D-citrulline.

Dose-Response of Microvascular Contractility to PGF$_{2\alpha}$ in the Presence and Absence of Inhibitors The dose-response curves of microvascular contractility to PGF$_{2\alpha}$ in the presence/absence of THG113 and its derivatives (10 µM) was determined in the porcine eye cup assay (Li et al. 1996) (FIG. 6A). All compounds inhibited PGF$_{2\alpha}$-induced responses even at high concentrations of the agonist. The inhibitory response of increasing doses of THG113 and its derivatives on porcine ocular contractility induced by 1 µM PGF$_{2\alpha}$ is shown in FIG. 6B. Both derivatives, 113.29 and 113.31, were more potent than the parent peptide (IC$_{50}$: 27 and 13 nM respectively).

Effect of THG113.31 on Contractile Properties of Uterine Strips

A dose-dependent reduction of uterine contractile responses (contraction duration and mean force of contraction), induced by the natural FP agonist, PGF$_{2\alpha}$, were observed in uterine strips obtained from recently-delivered mice in response to 1 µM PGF$_{2\alpha}$ in an organ bath assay (FIG.

7). This data confirmed that THG113.31, like the parent lead was effective in diminishing the contractility in myometrim in active state of labor. Reductions of similar magnitude were obtained in myometrial strips obtained from bovine and ovine animals. These data underscore the efficacy of THG113 inhibition in myometria from several distantly related species and the universal importance of FP receptor in myometrial contractility.

Tocolytic Effect of THG113.31 in an Endotoxin Model of Mouse Preterm Labor

Figure 8A:
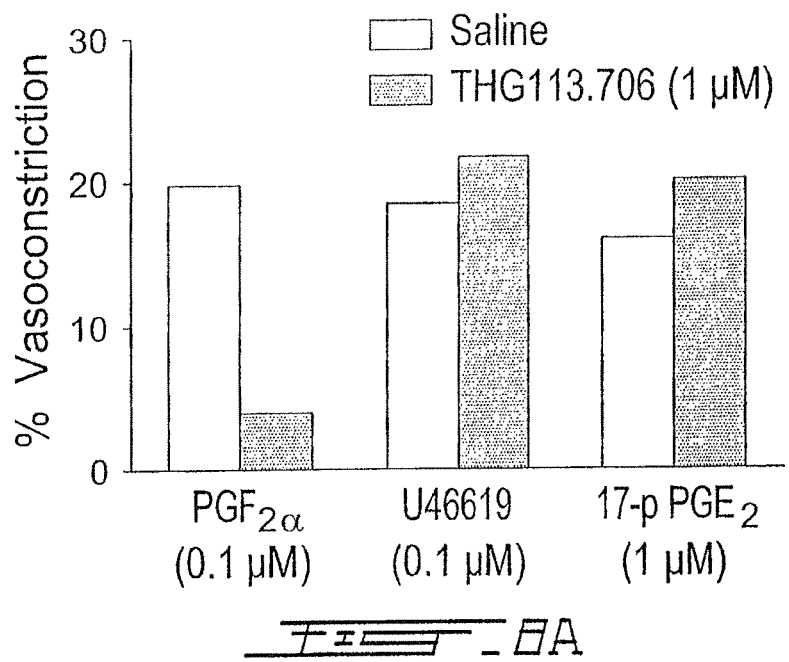
FIGS. 8A and B show the specificity of THG113.706 towards FP receptor in contractility assays.
Figure 8B:
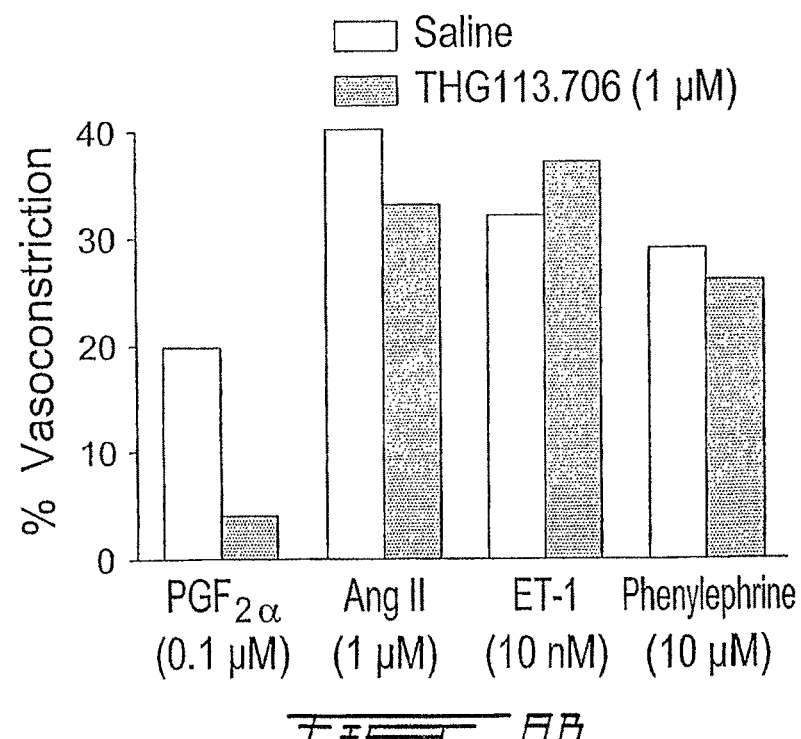

*E. coli* LPS (50 μg twice three hours apart, i.p) was administered to CD-1 mice (average weight: 50 g) at gestation day 15. Four hours after LPS was administered, alzet osmotic pumps that delivered 0.1, 0.4 or 0.8 mg/Kg/day of the drug were surgically implanted on the backs of the animals. Normal gestation in this strain is 19.2 days. The results are plotted graphically as mean time (h) of delivery after LPS administration (FIG. 8A) and percentage of animals delivered at 15, 24, 48, 72 h after LPS administration (FIG. 8B). All the saline-treated animals delivered within 15 h after LPS administration, whereas less than 30% and 15% of animals administered 0.1 mg and 0.8 mg, respectively delivered. There was dose-dependent delay in delivery. However, the differences in delay between the 0.4 and 0.8 mg doses were not statistically significant. At 0.4 and 0.8 mg doses, less than 50-60% of the animals delivered at 48 h after LPS administration. These data emphasize that THG113.31 is a potent tocolytic in an animal model in which the infectitious component of human preterm labor was mimicked.

Structure-Activity Analysis of the Peptidomimetics (3S,6S,7S,9S)-benzylindolizidinone (BnIAA) or (3S,6S, 9S)-indolizidinone (IAA) beta turn mimetic was used to construct several mimics of THG113 as shown in Table 5. The peptidomimetics were tested in the porcine microvascular contraction assay (Li at al. 1996).

Percent (%) inhibition denotes porcine ocular microvessel contraction in response to 100 nM $PGF_{2\alpha}$ in the presence of 0.1 mM peptide relative to that in the absence of the peptide, expressed as percentage.

TABLE 5

Structure-activity analysis of FP receptor inhibitor peptidomimetics

| Compound No. | Compound name | Structure | % inhibition |
|---|---|---|---|
| 33 | THG113.561 (50 μM) | E1-BnIAA-RD-N1 | 62.2 |
| 34 | THG113.562 (50 μM) | E1-BnIAA-RD-N2 | 63.2 |
| 35 | THG113.563 (50 μM) | E2-BnIAA-RD-N1 | 53.6 |
| 36 | THG113.564 (50 μM) | E2-BnIAA-RD-N2 | 81.1 |
| 37 | THG113.594 (100 μM) | E2-BnIAA-RD-N3 | 86.1 |
| 38 | THG113.595 (100 μM) | E2-BnIAA-RD-N4 | 46.8 |
| 39 | THG113.596 (100 μM) | E3-BnIAA-RD-N2 | 32.2 |
| 40 | THG113.654 (100 μM) | E2-IAA-RD-N3 | 85.9 |
| 41 | THG113.677 (100 μM) | E2-BnIAA-R-N5 | 59.0 |
| 42 | THG113.678 (100 μM) | E2-BnIAA-R-N6 | 66.8 |
| 43 | THG113.679 (100 μM) | E2-BnIAA-R-N7 | 75.6 |
| 44 | THG113.680 (100 μM) | E2-BnIAA-R-N9 | 58.0 |
| 45 | THG113.704 (100 μM) | E2-IAA-R-N8 | 61.8 |
| 46 | THG113.705 (100 μM) | E2-IAA-R-N5 | 51.1 |
| 47 | THG113.706 (100 μM) | E2-IAA-R-N9 | 80.4 |
| 48 | THG113.707 (100 μM) | E2-IAA-R-N7 | 68.0 |
| 49 | THG113.708 (100 μM) | E2-IAA-R-N6 | 59.5 |
| 50 | THG113.823 (100 μM) | E2-IAA-(Cit)-N9 | 73.0 |
| 51 | THG113.824 (100 μM) | E2-IAA(3PA)-N9 | 98.6 |
| 52 | THG113.825 (100 μM) | E2-IAA-(4PA)-N9 | 91.0 |

BnIAA = (3S,6S,7S,9S)-benzylindolizidinone;
IAA = (3S,6S,9S)-Indolizidinone;
Y1 = Cyclohexyl-CO—;
Z1 = i-BuNH—;
Y2 = $PhCH_2CO$—;
Z2 = $(Ph)_2CHCH_2CH_2NH$—;
Y3 = PhCO—;
Z3 = $PhCH_2NH$—;
Z4 = $PhCH_2CH_2NH$—;
Z5 = L-Phe;
Z6 = D-β homophe;
Z7 = L-βhomophe;
Z8 = $(Ph)_2CHCH_2CH_2NH$—;
Z9 = L-β-Phe Potency and Efficacy of Inhibition by Peptidomimetics Table 6 shows the potency and efficacy of inhibition of FP-mediated contractile responses by peptidomimetics of THG113 in porcine ocular microvessels. The percent (%) inhibition denotes porcine ocular microvessel contraction in response to 100 nM $PGF_{2\alpha}$ in the presence of 0.1 mM peptide (maximal response) relative to that in the absence of the peptide, expressed as percentage. $IC_{50}$ values represent the concentration of the compound at which 50% inhibition in microvascular contraction, elicited by 100 nM $PGF_{2\alpha}$, was produced.

TABLE 6

Potency and efficacy of inhibition of FP-mediated contractile response

| Compound No. | Compound name | $IC_{50}$ (nM) | Efficacy (% inhibition) |
|---|---|---|---|
| 1 | THG113 | 340 | 80.0 |
| 37 | THG113.594 | 13.6 | 86.1 |
| 40 | THG113.654 | 67.6 | 85.1 |
| 47 | THG113.706 | 1.6 | 80.4 |
| 48 | THG113.707 | 3.5 | 68.0 |
| 50 | THG113.823 | 2.5 | 73.0 |
| 51 | THG113.824 | 1.1 | 98.6 |
| 52 | THG113.825 | 61.5 | 91.0 |

Specificity of THG113.706 Towards FP Receptor in Contractility Assays

The specificity of THG113.706 towards FP receptor in contractility assays is shown in FIG. 9. Percent vasoconstriction denotes porcine ocular microvessel contraction in response to 100 nM $PGF_{2\alpha}$ in the presence of 1 µM peptide relative to that in the absence of the peptide, expressed as percentage. Concentrations of agonists of FP ($PGF_{2\alpha}$), TP (U46619), EP1 (17-phenyl $PGE_2$), angiotensin AT1 (Ang 11), endothelin receptor (ET-1) and alpha adrenergic receptors (phenylephrine) are indicated in parenthesis in the figure. THG113.31 did not affect the vasomotor responses produced by agonists of other GPCRs known to exist in vascular smooth muscle, including the highly homologous prostanoid receptors TP and EP1. As it was in the case with the parent peptide THG113, THG113.31 was found to be a selective inhibitor of FP receptor.

Tocolytic Effect of THG113.706 in a Endotoxin Model of Mouse Preterm Labor

*E. coli* LPS (50 µg twice three hours apart, i.p) was administered to CD-1 mice at gestation day 15. Alzet osmotic pumps that delivered 0.1 mg/Kg/day of the drug were surgically implanted on the backs of the animals. Normal gestation in this strain is 19.2 days. FIG. 10A shows the percentage of animals delivered after 15 h (left panel) and between 24 and 48 h (right panel) after LPS administration. Less than 25% of the animals delivered compared to all the saline-treated mice within the first 15 h after endotoxin administration. The inhibition (% of maximal contraction produced by 100 nM $PGF_{2\alpha}$) by a dose range of THG113.823-5 in porcine eye cup assays is shown in FIG. 10B. Of these three compounds, THG113.824 was found to be a very potent inhibitor of FP receptor ($IC_{50}$: 1.1 nM) while maintaining high efficacy of inhibition (>85%). This compound is over 300 fold more potent than the parent compound, THG113.

Chemical Synthesis of Peptides

Using F-moc chemistry (Wellings and Atherton (1997) Methods in Enzymology 289:44-66; Guy and Fields (1997) Methods in Enzymology 289:67-83) and solid phase Merrifield method (Merrifield (1963) J. Am. Chem. Soc. 85: 2149-2154), we have synthesized an L-peptide and several D-peptides (compounds 1 to 32, Table 4) which are 8 amino acids in length. The purity of these peptides was assessed by HPLC and mass spectroscopy.

The methods involved in synthesizing compounds 33-50 are outlined below.

Preparations

P-Nitrobenzophenone Oxime Resin (Findeis and Kaiser (1989) J. Org. Chem. 54: 3478-3482) Polystyrene (Bio-Beads S-X1, 200-400 mesh, 1% divinylbenzene, 25.0 g) was swollen in 200 mL of DCM for 30 min and then treated dropwise over 40 min with a solution of $AlCl_3$ (5.0 g, 37.5 mmol) and p-nitrobenzoyl chloride (5.0 g, 27 mmol) in 250 mL of DCM. The mixture was slowly stirred using an overhead stirrer for 72 h. The resin was placed on a coarse fritted glass filter, washed with 700 mL of dioxane:4 N HCl (3:1 v/v), 400 mL of dioxane:$H_2O$ (3:1 v/v), 400 mL of DMF, 400 mL of methanol, 200 mL of DCM and dried on a vacuum pump. The resulting resin was then suspended in 400 mL of ethanol, treated with pyridine (38 mL) and hydroxylamine hydrochloride (25 g, 0.36 mol) and heated at 90-95° C. for 24 h with slow stirring. The resin was placed on a coarse fritted glass filter and washed with 400 mL of methanol then dried on a vacuum pump. The substitution level of the resin was ascertained as described by Thouin and Lubell (Thouin and Lubell (2000) *Tetrahedron Lett.* 41: 457-460).

General Protocol for Linkage of Amino Acid and Carboxylic Acids onto Oxime Resin Swelled oxime resin (1.0 g) in 15 mL of DCM was treated with the carboxylic acid moiety, N-BOC-L-Asp(Chx)-OH (442 mg, 1.4 mmol), DCC (288 mg, 1.4 mmol) and EACNOx (398 mg, 2.8 mmol), stirred at room temperature for 24 h as described by Thouin and Lubell (2000) *Tetrahedron Lett.* 41: 457-460) and filtered. After filtration, the resin was washed with DCM (2×10 ml), DMF (2×10 ml), DCM (1×10 ml), DOM:isopropanol (1:1 v:v, 2×10 ml), DCM (3×10 ml) and dried under vacuum. Resin substitution was determine to be 0.74 mmol/g by displacing the amino acid with isobutylamine to provide the respective isobutylamide that was weighed and demonstrated to be of high purity by proton NMR or analytical HPLC. The free oxime sites were capped by treatment of the swelled resin in DOM (15 ml) with $Ac_2O$ (0.20 ml, 2.2 mmol) and DIEA (0.175 ml, 1.1 mmol), with stirring at room temperature for 12 h. The filtered resin was washed with DCM (2×10 ml), DCM:isopropanol (1:1 v:v, 2×10 ml), DCM (3×10 ml) and dried under vacuum.

General Protocol for Deprotection and Free Basing of the Oxime-Resin-Bound N-(Boc)Amino Group The BOC-protected oxime resin was treated with the following solutions (15 ml/g of resin) for the specified times: DCM:TFA (3:1 v:v, 1×2 min and 2×15 min), DCM (5×1 min), DCM:DIEA (2×2 min), DCM (3×1 min) and dried under vacuum (Thoulin and Lubell (2000) Tetrahedron Lett. 41:249-256).

General Protocol for Couplings with Amino Acid and Carboxylic Acids to Oxime-Resin-Bound Amine (Thoulin and Lubell (2000) Tetrahedron Lett. 41:249-256) The BOO group was removed and the amino resin was liberated using the protocol described above. A suspension of the resin amine was then submitted to a 2 h coupling with the respective carboxylic acid (1.1 equ.), TBTU (1.2 equ.) and DIEA (2.5 equ.) in 15 mL of DMF/g of resin. After filtration, the resin was washed (10 mL/g of resin) with DMF (2×1 min), DOM (1×1 min), DCM:isopropanol (1:1 v:v, 2×1 min), DOM (3×1 min) and dried under vacuum. The extent of coupling was evaluated by quantitative ninhydrin test.

General Protocol for the Nucleophilic Displacement of Protected Mimics from Oxime Resin (Thoulin and Lubell (2000) Tetrahedron Lett. 41:249-256) Samples of the resin-bound active ester, E-BnIAA-R(Mts)-D (Chx)-oxime resin, were treated for 24-48 h at room temperature with nucleophile (5-10 equ.) in $CHCl_3$ (15 mL/g of resin) containing 1% acetic acid. After filtration, the resin was washed (10 mL/g of resin) with $CHCl_3$ and $CHCl_3$:methanol (3:1 v/v) and the combined filtrates were evaporated to dryness. The crude products were purified by column chromatography with silica gel using a gradient of $CHCl_3$ with 1-3% as eluant or by reverse-phase (RP)HPLC on a C-18, 20×250 mm Higgins column using a gradient of 10:90 to 90:10 acetonitrile:water with 0.003% TFA in acetonitrile and 0.05% TFA in water for 40 min with a flow rate of 15.0 ml/min at detection at 214 nm. Analysis of the collected fractions was performed on an analytical C-18, 4.7×250 mm Higgins column using a gradient of 5:95 to 90:10 acetonitrile:water with 0.003% TFA in acetonitrile and 0.05% TFA in water for 30 min with a flow rate of 1.5 ml/min at detection at 214 nm.

General Protocol for Final Deprotection of Mimics (Stewart (1997) Methods in Enzymology 289: 29-44) Samples of the protected mimic, E-BnIAA-R(Mts)-D(Chx)-N, in TFA (40 µl/µmol) were treated with thioanisole (60 equ.) and m-cresol (15 equ.), cooled to 0° C., treated with TMSOTf (60 equ.), and stirred at 0° C. for 2 h and then at room temperature (RT) for 2 h. Cold $Et_2O$ (10 volumes) was added to the mixture and the precipitate was isolated by centrifugation. The solution was decanted and the solids were washed with cold $Et_2O$, dissolved in a minimum volume of methanol. The solids were treated with cold $Et_2O$ (10 volumes) again, isolated by centrifugation, washed with cold $Et_2O$ and dried under vacuum. The deprotected products were examined by analytical HPLC and purified by RP HPLC using conditions as described above.

Preparation of HCl Salts

Samples of TFA salt (x mmol) were dissolved in dioxane (500 µl/µmol), treated with concentrated HCl (12N, 200 µl/µmol) and evaporated to dryness to give the HCl salt as judged by the absence of the trifluoroacetate signal in the $^{19}F$ NMR spectrum (Gill and Lubell (1995) *J. Org. Chem.* 60:2658-2659). Compounds were judged to be of high purity by reverse-phase HPLC analysis using conditions described above.

Compounds Prepared

Compound 33: (3S,6S,7S,9S)-2-oxo-3-cyclohexanecarboxamido-7-benzyl-1-azabicyclo[4.3.0]nonane-9-carboxyl-L-argininyl-L-aspartyl-iso-butylamide trifluoroacetate (THG113.561): m/z 725 ($MH^+$).

Compound 34: (3S,6S,7S,9S)-2-oxo-3-cyclohexanecarboxamido-7-benzyl-1-azabicyclo[4.3.0]nonane-9-carboxyl-L-argininyl-L-aspartyl-3',3'-diphenylpropylamide trifluoroacetate (THG113.562): m/z 863 ($MH^+$).

Compound 35: (3S,6S,7S,9S)-2-oxo-3-phenylacetamido-7-benzyl-1-azabicyclo[4.3.0]nonane-9-carboxyl-L-argininyl-L-aspartyl-iso-butylamide trifluoroacetate (THG113.563): m/z 733 ($MH^+$).

Compound 36: (3S,6S,7S,9S)-2-oxo-3-phenylacetamido-7-benzyl-1-azabicyclo[4.3.0]nonane-9-carboxyl-L-argininyl-L-aspartyl-3',3'-diphenylpropylamide trifluoroacetate (THG113.564): m/z 871 ($MH^+$).

Compound 37: (3S,6S,7S,9S)-2-oxo-3-phenylacetamido-7-benzyl-1-azabicyclo[4.3.0]nonane-9-carboxyl-L-argininyl-L-aspartyl-benzylamide trifluoroacetate (THG113.594): m/z 767 ($MH^+$); HRMS Calcd for $C_{41}H_{51}N_8O_7$ ($MH^+$) 767.3881. found 767.3857. Tr=16.85 min.

Compound 38: (3S,6S,7S,9S)-2-Oxo-3-phenylacetamido-7-benzyl-1-azabicyclo[4.3.0]nonane-9-carboxyl-L-argininyl-L-aspartyl-2'-phenylethylamide trifluoroacetate (THG113.595): m/z 781 ($MH^+$).

Compound 39: (3S,6S,7S,9S)-2-Oxo-3-benzamido-7-benzyl-1-azabicyclo[4.3.0]nonane-9-carboxyl-L-argininyl-L-aspartyl-3',3'-diphenylpropylamide trifluoroacetate (THG113.596): m/z 857 ($MH^+$).

Compound 40: (3S,6S,9S)-2-oxo-3-phenylacetamido-1-azabicyclo[4.3.0]nonane-9-carboxyl-L-argininyl-L-aspartyl-benzylamide trifluoroacetate (THG113.654): m/z 677 ($MH^+$); HRMS Calcd for $C_{34}H_{45}N_8O_7$ ($MH^+$) 677.3411. found 677.3424. Tr=13.56 min.

Compound 41: (3S,6S,7S,9S)-2-oxo-3-phenylacetamido-7-benzyl-1-azabicyclo[4.3.0]nonane-9-carboxyl-L-argininyl-L-phenylalanine trifluoroacetate (THG113.677): m/z 710 ($MH^+$); $^1H$ NMR ($CD_3OD$, 400 MHz) δ 1.55-1.95 (m, 9H), 2.05 (m, 1H), 2.33 (m, 1H), 2.63 (dd, 1H, J=13.9, 8.2), 2.82 (dd, 1H, J=13.4, 6.0), 2.95 (dd, 1H, J=14.1, 8.6), 3.07 (t, 2H, J=7.0), 3.18 (dd, 1H, J=13.8, 4.8), 3.47 (m, 1H), 3.51 (s, 2H), 4.35 (m, 2H), 4.44 (t, 1H, J=5.2), 4.64 (dd, 1H, J=8.5, 5.1), 7.07-7.30 (m, 15H).

Compound 42: (3S,6S,7S,9S)-2-Oxo-3-phenylacetamido-7-benzyl-1-azabicyclo[4.3.0]nonane-9-carboxyl-L-argininyl-(3'R)-3'-amino-5'-phenylpentanoic acid trifluoroacetate (THG113.678): m/z 738 ($MH^+$); $^1H$ NMR ($CD_3OD$, 400 MHz) δ1.55-1.90 (m, 10H), 1.99 (dd, 2H, J 8.9, 4.9), 2.10 (m, 1H), 2.25 (m. 1H), 2.45-2.63 (m, 4H), 2.82 (m, 1H), 3.09 (t, 2H, J=7.0), 3.37 (m, 1H), 3.53 (d, 2H, J=3.5), 4.15 (m, 1H), 4.22 (m, 1H), 4.27 (m, 1H), 4.40 (m, 1H), 7.07-7.30 (m, 15H).

Compound 43: (3S,6S,7S,9S)-2-oxo-3-phenylacetamido-7-benzyl-1-azabicyclo[4.3.0]nonane-9-carboxyl-L-argininyl-(3'S)-3'-amino-5'-phenylpentanoic acid trifluoroacetate (THG113.679): m/z 738 ($MH^+$); $^1H$ NMR ($CD_3OD$, 400 MHz) δ1.55-1.90 (m, 10H), 1.91-2.10 (m, 3H), 2.28 (m, 1H), 2.40-2.67 (m, 4H), 2.75 (m, 1H), 3.10 (t, 2H, J=7.0), 3.37 (m, 1H), 3.50 (s, 2H), 4.19 (m, 1H), 4.25 (m, 1H), 4.40 (m, 2H), 7.03-7.30 (m, 15H).

Compound 44: (3S,6S,7S,9S)-2-oxo-3-phenylacetamido-7-benzyl-1-azabicyclo[4.3.0]nonane-9-carboxyl-L-argininyl-(3'S)-3'-amino-4'-phenylbutanoic acid trifluoroacetate (THG113.680): m/z 724 ($MH^+$); $^1H$ NMR ($CD_3OD$, 400 MHz) δ1.50-2.00 (m, 9H), 2.07 (m, 1H), 2.25-2.50 (m, 3H), 2.62 (m, 1H), 2.70-2.90 (m, 3H), 3.05 (t, 2H, J=6.9), 3.36 (m, 1H), 3.50 (d, 2H, J=4.0), 4.25 (m, 1H), 4.33-4.46 (m, 3H), 7.05-7.30 (m, 15H).

Compound 45: (3S,6S,9S)-2-oxo-3-phenylacetamido-1-azabicyclo[4.3.0]nonane-9-carboxyl-L-argininyl-3'-phenylpropylamide trifluoroacetate (THG113.704): m/z 590 ($MH^+$); $^1H$ NMR ($CD_3OD$, 400 MHz) δ1.55-1.93 (m, 10H), 1.99-2.28 (m, 5H), 2.62 (t, 2H, J=7.2), 3.23 (m, 1H), 3.50 (s, 2H), 3.67 (m, 1H), 4.24 (m, 2H), 4.40 (d, 1H, J=10.0), 7.10-7.30 (m, 10H).

Compound 46: (3S,6S,9S)-2-oxo-3-phenylacetamido-1-azabicyclo[4.3.0]nonane-9-carboxyl-L-argininyl-L-phenylalanine trifluoroacetate (THG113.705): m/z 620 ($MH^+$); $^1H$ NMR ($CD_3OD$, 400 MHz) δ1.57-1.93 (m, 8H), 2.00-2.18 (m, 4H), 3.00 (dd, 1H, J=14.0, 8.5), 3.10 (t, 2H, J=7.0), 3.22 (dd, 1H, J=13.8, 4.9), 3.53 (s, 2H), 3.65 (m, 1H), 4.35 (m, 2H), 4.47 (t, 1H, J=5.1), 4.67 (dd, 1H, J=8.4, 5.1), 7.15-7.32 (m, 10H).

Compound 47: (3S,6S,9S)-2-oxo-3-phenylacetamido-1-azabicyclo[4.3.0]nonane-9-carboxyl-L-argininyl-(3'S)-3'-amino-4'-phenylbutanoic acid trifluoroacetate (THG113.706): m/z 634 ($MH^+$); HRMS Calcd for $C_{33}H_{44}N_7O_6$ ($MH^+$) 634.33533. found 634.33350. Tr=14.23 min, $^1H$ NMR ($CD_3OD$, 400 MHz) δ1.55-2.22 (m, 12H), 2.50 (m, 2H), 2.87 (d, 2H, J=7.3), 3.09 (m, 2H), 3.53 (d, 2H, J=3.4), 4.28 (m, 1H), 4.40 (m, 3H), 7.17-7.32 (m, 10H).

Compound 48: (3S,6S,9S)-2-oxo-3-phenylacetamido-1-azabicyclo[4.3.0]nonane-9-carboxyl-L-argininyl-(3'S)-3'-amino-5'-phenylpentanoic acid trifluoroacetate (THG113.707): m/z 648 ($MH^+$); $^1H$ NMR ($CD_3OD$/400 MHz) δ1.60-1.91 (m, 9H), (m, 5H), 2.45-2.73 (m, 4H), 3.13 (t, 2H, J=7.0), 3.49 (s, 2H), 3.65 (m, 1H), 4.21 (m, 1H), 4.29 (m, 1H), 4.40 (m, 2H), 7.10-7.30 (m, 10H).

Compound 49: (3S,6S,9S)-2-oxo-3-phenylacetamido-1-azabicyclo[4.3.0]nonane-9-carboxyl-L-argininyl-(3'R)-3'-amino-5'-phenylpentanoic acid trifluoroacetate (THG113.708): m/z 648 ($MH^+$); $^1H$ NMR ($CD_3OD$, 400 MHz) δ1.60-1.95 (m, 9H), 2.00-2.30 (m, 5H), 2.50-2.75 (m, 4H), 3.11 (t, 2H, J=7.0), 3.56 (d, 2H, J=3.7), 3.68 (m, 1H), 4.15-4.30 (m, 3H), 4.43 (d, 1H, J=9.4), 7.10-7.35 (m, 10H).

Compound 50: (3S,6S,9S)-2-oxo-3-phenylacetamido-1-azabicyclo[4.3.0]nonane-9-carboxyl-L-citrulinyl-(3'S)-3'-amino-4'-phenylbutanoic acid trifluoroacetate (THG113.823): m/z 635 (MH+); HRMS Calcd for C33H43N6O7 (MH+) 635.3193. found 635.3176. Tr=15.16 min; $^1H$ NMR (CD3OD, 400 MHz) δ 1.53-1.85 (m, 7H), 1.95-2.20 (m, 5H), 2.47 (m, 2H), 2.84 (d, 2H, J=6.95), 3.07 (m, 2H), 3.53 (s, 2H), 3.67 (m, 1H), 4.25 (m, 1H), 4.43 (m, 3H), 7.15-7.30 (m, 10H).

Compound 51: (3S,6S,9S)-2-oxo-3-phenylacetamido-1-azabicyclo[4.3.0]nonane-9-carboxyl-(3-pyridyl)-L-alaninyl-(3'S)-3'-amino-4'-phenylbutanoic acid trifluoroacetate (THG113.824): m/z 626 (MH+); HRMS Calcd for C35H40N5O6 (MH+) 626.2979. found 626.2965. Tr=14.25 min; 1H NMR (CD3OD, 400 MHz) δ 1.50 (m, 1H), 1.65-1.90 (m, 3H), 1.98-2.20 (m, 4H), 2.47 (m, 2H), 2.80-3.00 (m, 3H), 3.17 (m, 1H), 3.53 (m, 2H), 3.65 (m, 1H), 4.32 (m, 2H), 4.43 (m, 1H), 4.53 (m, 1H), 7.15-7.30 (m, 11H), 7.62 (m, 1H), 8.50 (m, 2H).

Compound 52: (3S,6S,9S)-2-Oxo-3-phenylacetamido-1-azabicyclo[4.3.0]nonane-9-caboxyl-(4-pyridyl)-L-alaninyl-(3'S)-3'-amino-4'-phenylbutanoic acid trifluoroacetate (THG113.825): m/z 626 (MH+): HRMS Calcd for C35H40N5O6 (MH+) 626.2979. found 626.2965; Tr=14.15 min; $^1$H NMR (CD3OD, 400 MHz) d 1.5 (m, 1H), 1.65-1.90 (m, 3H), 1.97-2.20 (m, 4H), 2.47 (m, 2H), 2.86 (m, 2H), 3.01 (m, 1H), 3.22 (m, 1H), 3.51 (m, 2H), 3.63 (m, 1H), 4.33 (m, 2H), 4.45 (m, 1H), 4.60 (m, 1H), 7.15-7.30 (m, 12H), 8.50 (m, 2H).

Structures of Peptidomimetics of THG113

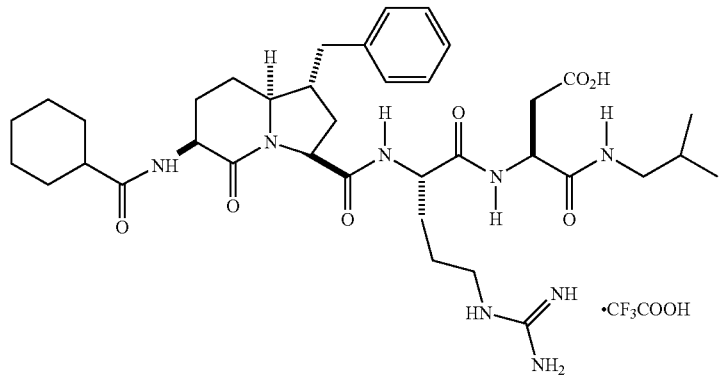

113.561

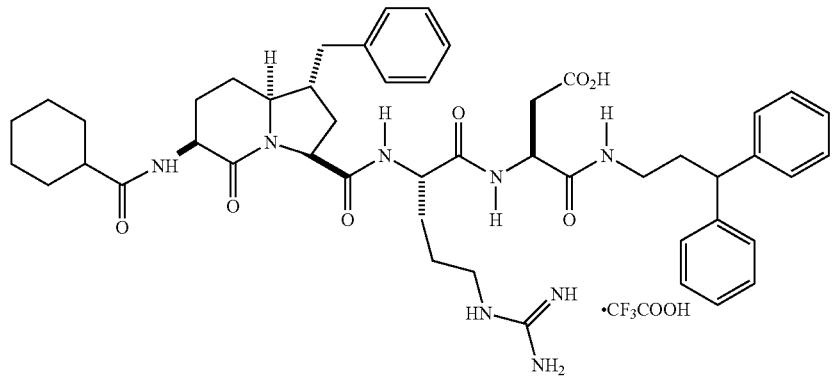

113.562

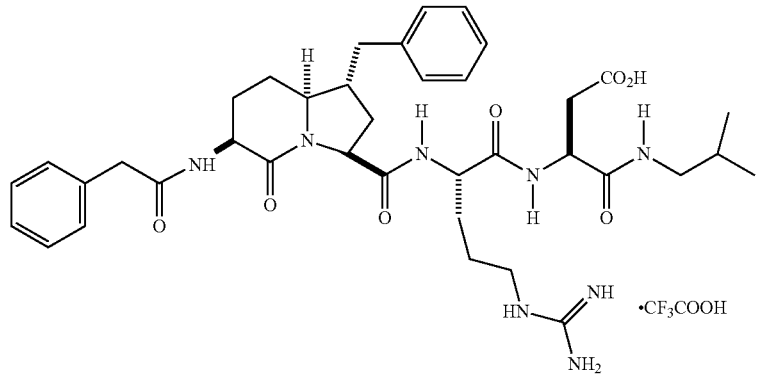

113.563

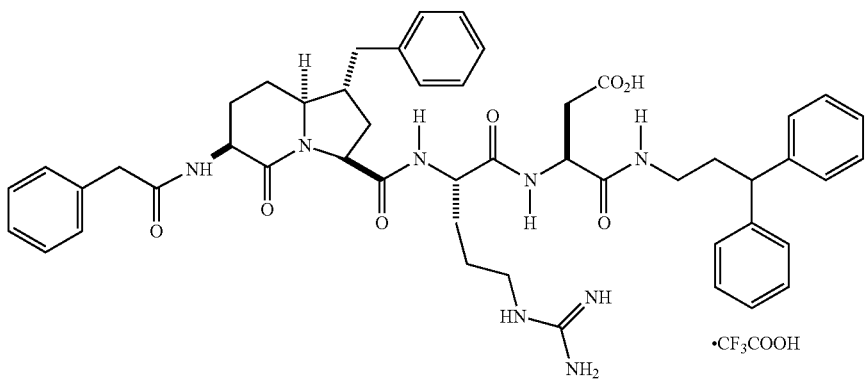
113.564
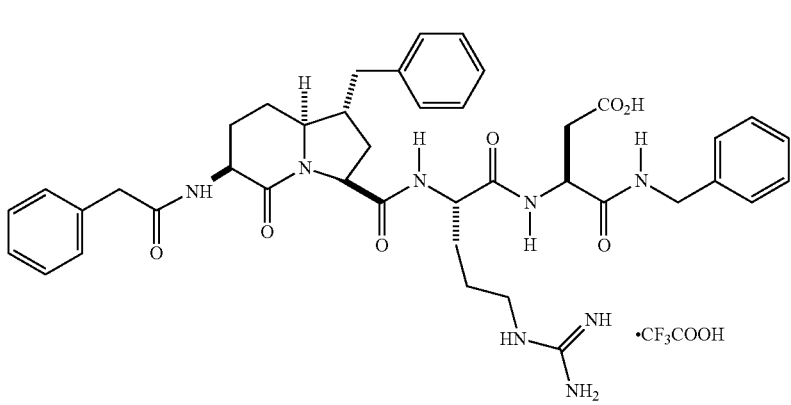
113.594
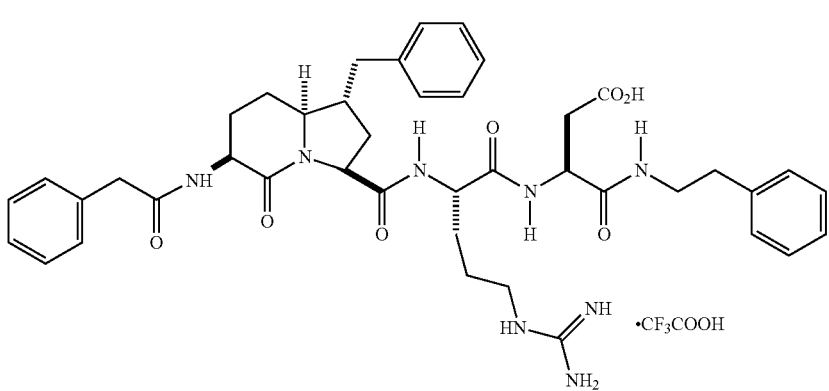
113.595

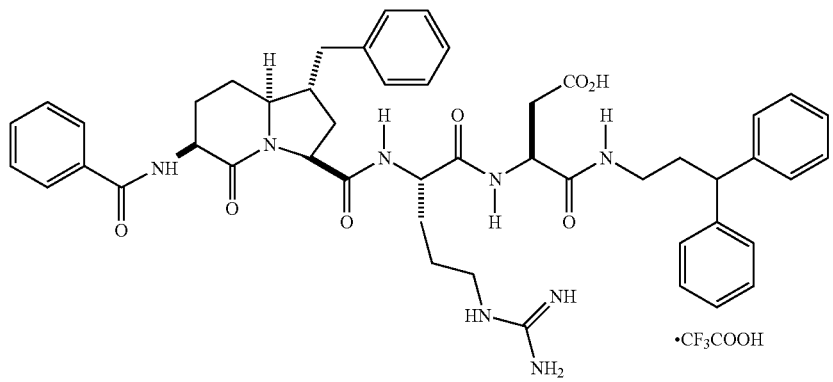
113.596
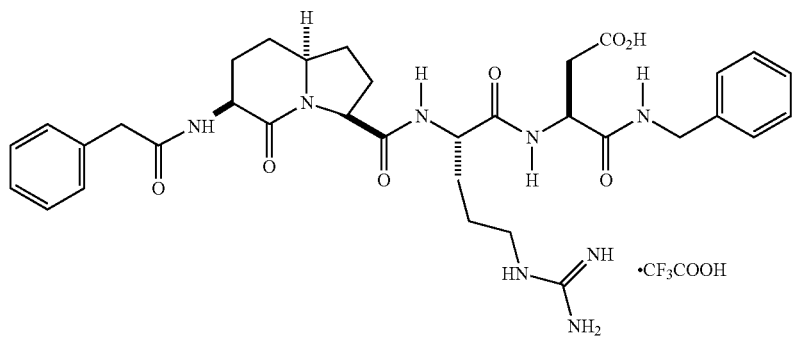
113.654
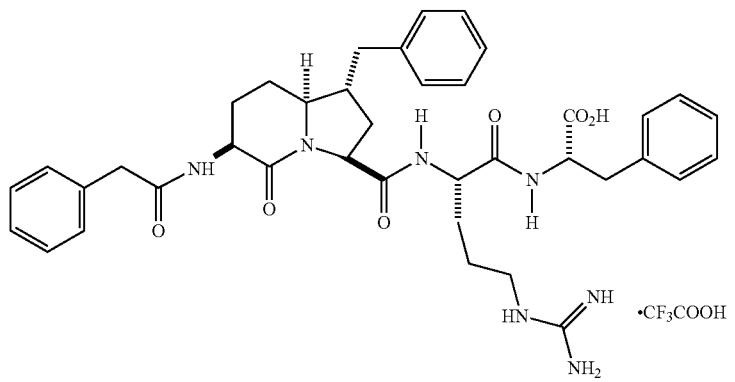
113.677

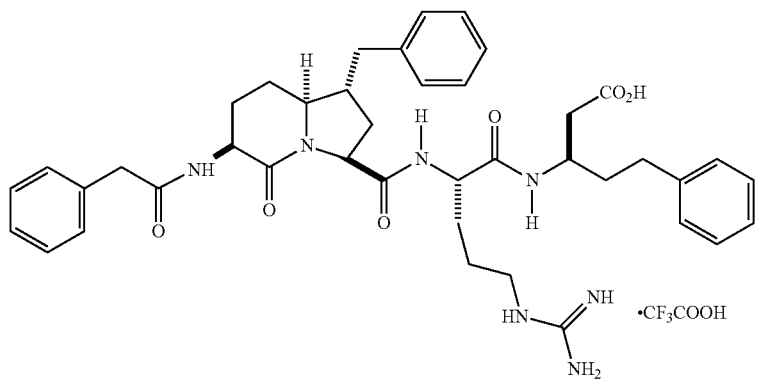
113.678
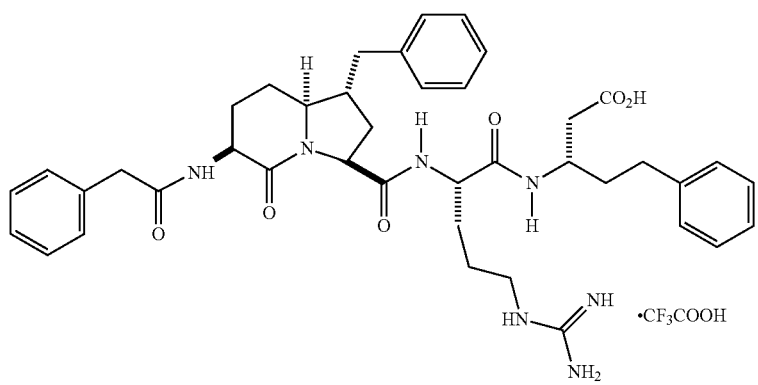
113.679
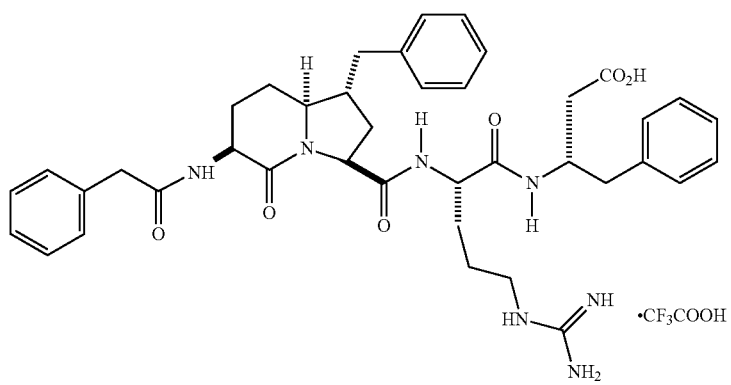
113.680

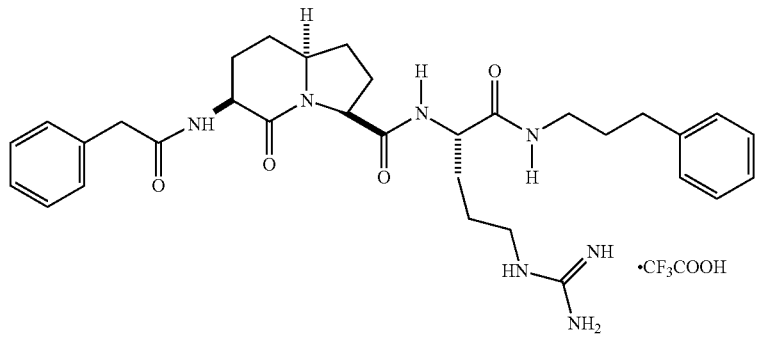
113.704
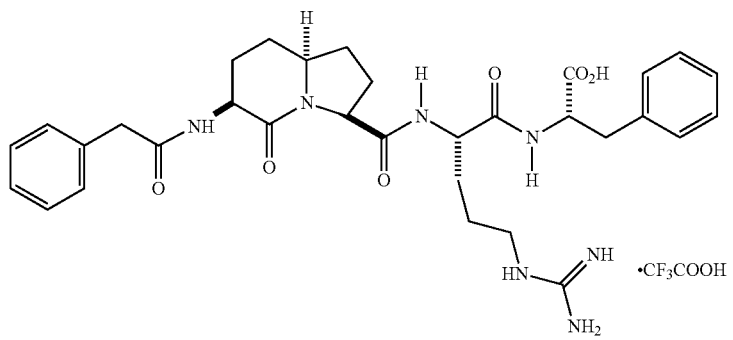
113.705
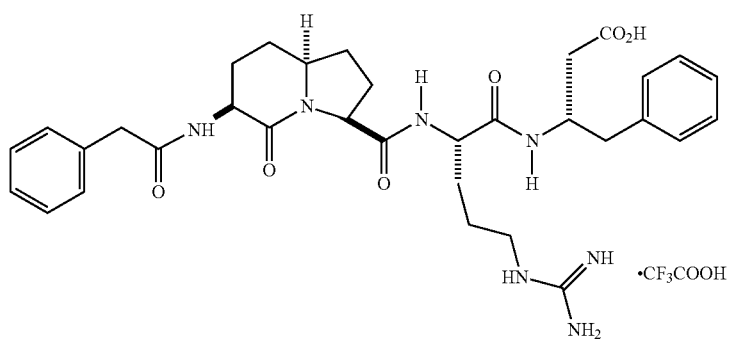
113.706
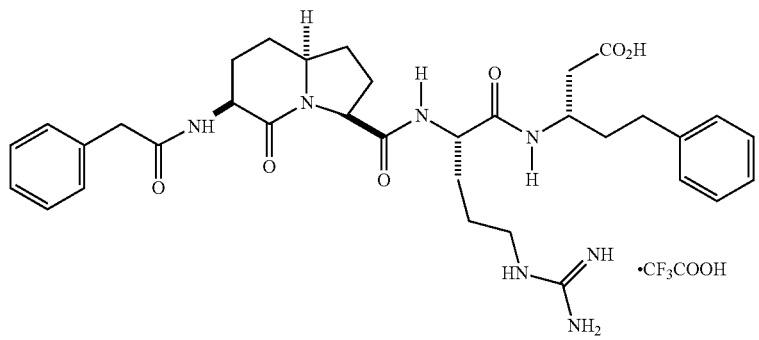
113.707

49
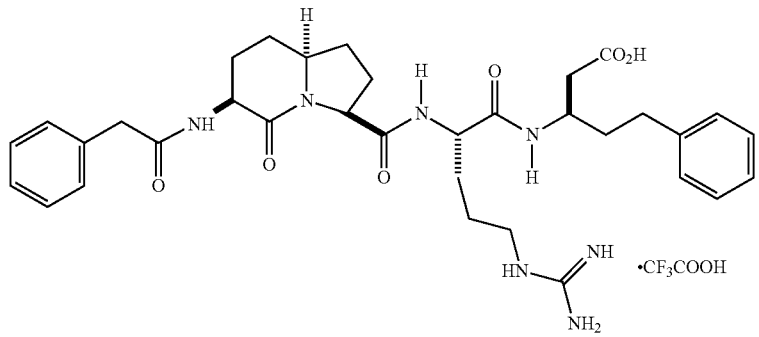
113.708
50
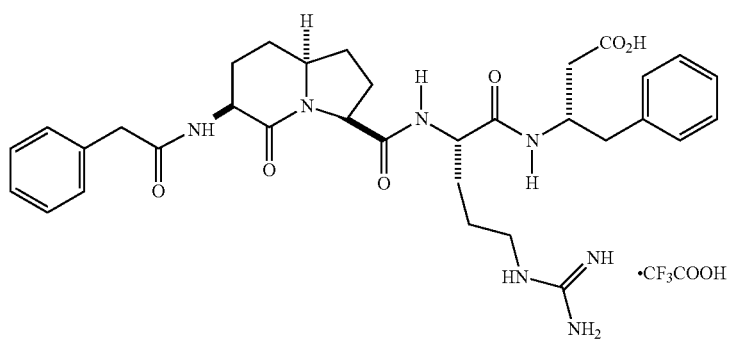
113.823
51
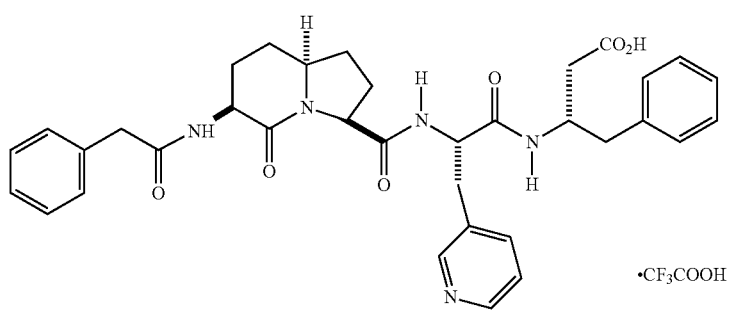
113.824
52
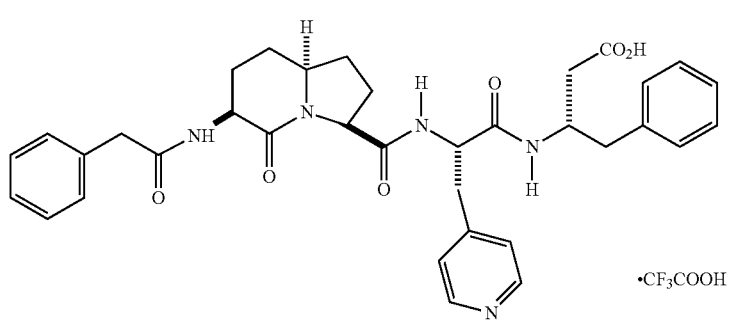
113.825

What is claimed is:

1. A peptidomimetic compound selected from the group consisting of:
(3S,6S,9S)-2-Oxo-3-phenylacetamido-1-azabicyclo[4.3.0]nonane-9-carboxyl-L-argininyl-(3'S)-3'-amino-4'-phenylbutanoic acid;
(3S,6S,9S)-2-Oxo-3-phenylacetamido-1-azabicyclo[4.3.0]nonane-9-carboxyl-L-citrulinyl-(3'S)-3'-amino-4'-phenylbutanoic acid;
(3S,6S,9S)-2-Oxo-3-phenylacetamido-1-azabicyclo[4.3.0]nonane-9-carboxyl-(3-pyridyl)-L-alaninyl-(3'S)-3'-amino-4'-phenylbutanoic acid;
(3S,6S,9S)-2-Oxo-3-phenylacetamido-1-azabicyclo[4.3.0]nonane-9-carboxyl-(4-pyridyl)-L-alaninyl-(3'S)-3'-amino-4'-phenylbutanoic acid; and
pharmaceutically acceptable salts thereof.

2. A compound in accordance with claim 1 wherein the peptidomimetic comprises (3S,6S,9S)-2-Oxo-3-phenylacetamido-1-azabicyclo[4.3.0]nonane-9-carboxyl-L-argininyl-(3'S)-3'-amino-4'-phenylbutanoic acid.

3. A compound in accordance with claim 1 wherein the peptidomimetic comprises (3S,6S,9S)-2-Oxo-3-phenylacetamido-1-azabicyclo[4.3.0]nonane-9-carboxyl-L-citrulinyl-(3'S)-3'-amino-4'-phenylbutanoic acid.

4. A compound in accordance with claim 1 wherein the peptidomimetic comprises (3S,6S,9S)-2-Oxo-3-phenylacetamido-1-azabicyclo[4.3.0]nonane-9-carboxyl-(3-pyridyl)-L-alaninyl-(3'S)-3'-amino-4'-phenylbutanoic acid.

5. A compound in accordance with claim 1 wherein the peptidomimetic comprises (3S,6S,9S)-2-Oxo-3-phenylacetamido-1-azabicyclo[4.3.0]nonane-9-carboxyl-(4-pyridyl)-L-alaninyl-(3'S)-3'-amino-4'-phenylbutanoic acid.

6. A pharmaceutical composition comprising a therapeutically effective amount of at least one compound of claim 1 in association with a pharmaceutically acceptable carrier.

7. A method of inhibiting Prostaglandin F (FP) receptor function in an individual in need thereof, the method comprising administering to such an individual an inhibitory amount of the pharmaceutical composition of claim 6.

8. The method of claim 7 wherein said receptor is from a mammal.

9. The method of claim 8 wherein said mammal is a human.

10. A method of treating preterm labor comprising administering to an individual the pharmaceutical composition of claim 6.

11. A method of treating dysmenorrhea comprising administering to an individual the pharmaceutical composition of claim 6.

* * * * *